(12) United States Patent
Herrmann

(10) Patent No.: US 12,721,959 B2
(45) Date of Patent: Sep. 1, 2026

(54) NEBULIZER WITH NON-DETACHABLY ATTACHED INDICATOR DEVICE

(71) Applicant: Boehringer Ingelheim International GmbH, Ingelheim am Rhein (DE)

(72) Inventor: Frank Herrmann, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 797 days.

(21) Appl. No.: 18/003,167

(22) PCT Filed: Jun. 30, 2021

(86) PCT No.: PCT/EP2021/067935
§ 371 (c)(1),
(2) Date: Dec. 23, 2022

(87) PCT Pub. No.: WO2022/002993
PCT Pub. Date: Jan. 6, 2022

(65) Prior Publication Data

US 2023/0277783 A1 Sep. 7, 2023

(30) Foreign Application Priority Data

Jul. 3, 2020 (EP) .................................... 20183947

(51) Int. Cl.
*A61M 15/00* (2006.01)

(52) U.S. Cl.
CPC .... *A61M 15/0073* (2014.02); *A61M 15/0081* (2014.02); *A61M 15/0086* (2013.01); *A61M 15/009* (2013.01)

(58) Field of Classification Search
CPC ...................... A61M 15/0073; A61M 15/0081
See application file for complete search history.

(56) References Cited

U.S. PATENT DOCUMENTS 5,069,204 A * 12/1991 Smith ............... A61M 15/0091 128/200.23
5,349,945 A * 9/1994 Wass ................ A61M 15/0068 128/200.14

(Continued)

FOREIGN PATENT DOCUMENTS

AU 2015202524 A1 5/2015
CN 217140807 U 8/2022

(Continued)

OTHER PUBLICATIONS

International Search Report and Written Opinion for corresponding PCT Application No. PCT/EP2021/067935, 12 pages, dated Sep. 24, 2021.

*Primary Examiner* — Kathryn E Ditmer
(74) *Attorney, Agent, or Firm* — Calderon Safran & Wright P.C.; David S. Safran

(57) ABSTRACT

A nebulizer for nebulizing a fluid is proposed. The nebulizer includes an indicator device with a rotatable indicator element for counting or indicating a number of actuations performed or still possible with the nebulizer and a rotatable shaft which rotatably drives the indicator element. The indicator device is non-detachably attached to the shaft and/or to an inner part of the nebulizer. The nebulizer may further include a positioning device that keeps the shaft in a defined rotational position and/or blocks the shaft from rotating backwards.

18 Claims, 7 Drawing Sheets

(56) References Cited

U.S. PATENT DOCUMENTS

| | | | | |
|---|---|---|---|---|
| 5,482,030 | A * | 1/1996 | Klein | A61M 15/0083 128/200.14 |
| 5,826,571 | A * | 10/1998 | Casper | A61M 15/0091 128/200.14 |
| 6,149,054 | A * | 11/2000 | Cirrillo | G06M 1/00 235/34 |
| 10,898,661 | B2 | 1/2021 | Jung | |
| 11,229,754 | B2 * | 1/2022 | Eicher | B05B 11/026 |
| 2002/0047021 | A1 * | 4/2002 | Blacker | G06M 1/041 222/23 |
| 2002/0195102 | A1 * | 12/2002 | Rand | A61M 15/0068 128/200.14 |
| 2006/0084908 | A1 * | 4/2006 | Bonney | A61M 15/009 128/200.24 |
| 2007/0062518 | A1 * | 3/2007 | Geser | A61M 15/0081 128/200.14 |
| 2007/0107720 | A1 * | 5/2007 | Boeck | A61M 15/009 128/200.14 |
| 2009/0272312 | A1 * | 11/2009 | Nuttall | A61M 15/009 116/299 |
| 2010/0282249 | A1 * | 11/2010 | Hately | A61M 15/0073 128/200.23 |
| 2012/0241526 | A1 * | 9/2012 | Kaar | A61M 15/0078 235/87 R |
| 2012/0241527 | A1 * | 9/2012 | Stuart | G06M 1/163 235/87 R |
| 2015/0040890 | A1 * | 2/2015 | Besseler | A61M 15/0038 128/200.14 |
| 2015/0320947 | A1 * | 11/2015 | Eicher | B05B 11/0054 128/200.14 |
| 2015/0320948 | A1 | 11/2015 | Eicher et al. | |
| 2017/0004395 | A1 * | 1/2017 | Smith | G06M 1/04 |
| 2017/0021117 | A1 * | 1/2017 | Howgill | G06M 1/166 |
| 2017/0361036 | A1 * | 12/2017 | Wang | A61M 15/008 |
| 2018/0228986 | A1 * | 8/2018 | Buck | A61M 15/0021 |
| 2019/0030268 | A1 | 1/2019 | Huang | |
| 2022/0047823 | A1 * | 2/2022 | Säll | B05B 11/1091 |
| 2022/0134027 | A1 * | 5/2022 | Zeng | G06M 1/045 116/311 |
| 2023/0277783 | A1 | 9/2023 | Herrmann | |
| 2023/0321365 | A1 * | 10/2023 | Tang | A61M 15/0081 128/200.14 |

FOREIGN PATENT DOCUMENTS

| | | | | |
|---|---|---|---|---|
| EP | 1369139 | A1 | 12/2003 | |
| EP | 2614848 | A1 | 7/2013 | |
| EP | 2835146 | A1 | 2/2015 | |
| GB | 2491611 | A * | 12/2012 | G06M 1/083 |
| WO | 2004024340 | A1 | 3/2004 | |
| WO | WO-2006062448 | A1 * | 6/2006 | A61M 15/0091 |
| WO | 2007022898 | A2 | 3/2007 | |
| WO | WO-2009086009 | A1 * | 7/2009 | A61M 15/0073 |
| WO | 2009115200 | A1 | 9/2009 | |
| WO | 2011064164 | A1 | 6/2011 | |
| WO | 2012162305 | A1 | 11/2012 | |
| WO | 2015018904 | A1 | 2/2015 | |
| WO | 2015169431 | A2 | 11/2015 | |
| WO | 2019016409 | A2 | 1/2019 | |

* cited by examiner 17
17A
33
17D
32A
17B
29B
17C
29D
27A
30C
23
30B
32
30
17E
27
25
29D 23
30D
30C
16A
6
34
3
16
17
7
9
16A
19

NEBULIZER WITH NON-DETACHABLY ATTACHED INDICATOR DEVICE

BACKGROUND

The present disclosure relates to a nebulizer.

WO 2011/064164 A1 discloses a nebulizer. A container can be inserted into a housing of the nebulizer. The housing is closed by a lower housing part. By rotating the housing part, a drive spring can be put under tension and fluid can be sucked into a compression chamber of a pressure generator. Simultaneously, the container is moved into the lower housing part in a stroke movement within the nebulizer. When moved for the first time, the container may be pierced through its base by a piercing element in the lower housing part to allow venting of the container. After manually pressing a button, the drive spring is released and moves a delivery tube into the pressure chamber so that the fluid is put under pressure by the drive spring and is delivered or atomized through a nozzle into a mouthpiece as an aerosol, without the use of propellant gas. Thus, the container is moving axially forth and back during conveying of the fluid to be nebulized, and during pressure generation and nebulization.

The known nebulizer comprises a threaded shaft with an associated non-rotatable rider. The threaded shaft is rotatably driven by the relative rotation of the housing part when tensioning the nebulizer. Rotating the threaded shaft causes the rider to axially move, wherein the axial position of the rider corresponds to the total number of operations or actuations of the nebulizer. When a certain number of actuations has been reached or exceeded, the rider can lock the nebulizer against further operation or use.

The known nebulizer further comprises a control ring which is rotatable and driven by the rotation of the threaded shaft. The control ring is located in the lower housing part and blocks the lower housing part from being detached until a predetermined number of operations has been reached. Further, the rotation position of the control ring corresponds to the number of operations or uses of the nebulizer with the current container and may be displayed or indicated by means of the control ring. When the predetermined number has been reached, the control ring unblocks the lower housing part. Then, the lower housing part, together with the control ring and the container, can be detached and replaced by a new lower housing part, new control ring and new container. Such replacement is possible until the nebulizer is permanently blocked by means of the rider.

WO 2007/022898 A2 discloses a similar nebulizer, wherein a first counter counts the number of operations with the current container and a second counter counts the total number of operations, thus, with several containers. The first counter comprises two count rings which are rotatably driven by a linear stroke movement of the container within the nebulizer. Further, the first counter drives the second counter. WO 2007/022898 A2 shows different embodiments in which the first counter is located at different positions within the lower housing part. However, it is essential for the first counter to be attached to the lower housing part in order to be detachable and replaceable together with the lower housing part when a new container is inserted.

WO 2012/162305 A1, US 2015/0040890 A1 and EP 2 835 146 A1 show a similar nebulizer, wherein a threaded shaft with associated only axially movable, non-rotatable rider is attached to the lower housing part such that it is replaceable together with the lower housing part when a new container is inserted. A ring-like indicator member is arranged at an upper housing part which indicates the number of containers that have been used or still can be used. The indicator member is driven by the force of a spring only when container replacement is due and/or when a container is replaced.

WO 2015/018904 A1 also discloses a nebulizer in which a threaded shaft is attached to a replaceable lower housing part. For preventing movement of the shaft before the lower housing part is connected to the nebulizer, the lower housing part comprises a blocking device which blocks the shaft in a defined rotational position until the nebulizer is closed. Upon closure of the nebulizer by attaching the lower housing part, the blocking device is axially moved such that, in this closed state, the blocking device no longer blocks rotation of the shaft.

WO 2015/169431 A2 shows a nebulizer in which an indicator device is directly attached to the base of the container. The indicator device shows the number of uses performed or still possible with the container. Since the indicator device is fixed to the container, it is necessarily replaced together with the container.

WO 2004/024340 A1 discloses a blocking device for permanently blocking a nebulizer against further use. The nebulizer is actuated by rotating two housing parts of the nebulizer relative to each other. The blocking device comprises a leaf spring which is initially accommodated within a recess of one of the housing parts in a pre-tensioned rest position. When the permitted number of operations with the nebulizer is achieved, a pin pushes the leaf spring out of its rest position, which causes the leaf spring to expand into a recess of the other housing part such that the housing parts can no longer be rotated relative to each other. This blocking can only be overcome by a force great enough to destroy the nebulizer.

SUMMARY

Object of the present disclosure is to provide a nebulizer allowing easy and/or improved handling and/or a simple or compact construction.

The above object is achieved by a nebulizer as disclosed herein.

The present disclosure relates to a nebulizer for nebulizing a fluid, preferably a liquid medicament, in particular from a container containing a fluid.

The nebulizer comprises an inner part and a lower housing part which can be detached from the inner part for opening the nebulizer, in particular for inserting the container.

The inner part is preferably cylinder-like or at least essentially formed as a (hollow) cylinder.

The nebulizer comprises an indicator device with a rotatable indicator element. The indicator device is constructed to count or indicate a number of actuations or uses performed or still possible with the nebulizer or the number of doses of fluid discharged or still possible to discharge. In particular, the indicator element comprises markings for indicating or showing these numbers, e.g. numerals and/or pitch lines.

In the sense of the present disclosure, an actuation is preferably an action or a series of actions a user has to perform to discharge or nebulize a dose of fluid such as, for example, loading an energy store of the nebulizer. Preferably, the number of actuations performed or still possible corresponds to or equals the number of doses of fluid discharged or still possible to discharge.

Preferably, the indicator element is indexed or stepwise rotated when the nebulizer is actuated, in particular when an energy store of the nebulizer is loaded and/or when a dose of fluid is discharged. For this purpose, the nebulizer comprises a rotatable shaft which rotatably drives the indicator element.

Preferably, the shaft and the indicator element are rotatably coupled with each other and/or a (partial) rotation of the shaft drives, indexes and/or (stepwise) rotates the indicator element.

Particularly preferably, the nebulizer is constructed such that the shaft performs a (partial) rotation when the nebulizer is actuated, which (partial) rotation, in turn, drives, indexes and/or (stepwise) rotates the indicator element.

The indicator element is preferably ring-like or formed as a (closed) ring.

The shaft is preferably attached to the inner part, in particular non-detachably, and/or the inner part comprises and/or bears the shaft.

According to an aspect of the present disclosure, the indicator device is non-detachably attached or connected to the inner part and/or the shaft. In this way, a very simple and robust construction is achieved. In particular, the rotational coupling of the shaft and the indicator element can already be provided in the delivery state of the nebulizer and, thus, a particularly easy handling is ensured. Moreover, by the non-detachable construction, it is ensured that the nebulizer can only be used with the indicator device and/or that the indicator device cannot be removed from the nebulizer, e.g. by a user, which is again conducive to an easy and/or secure handling.

The indicator device is preferably attached to a free or axial end of the inner part. This allows for a very compact construction and simple assembly.

Preferably, the nebulizer or inner part comprises a retaining part to which the indicator device is non-detachably attached and/or by which the indicator device is non-detachably retained. The retaining part may form part of the inner part and/or may be (non-detachably) attached or connected to the inner part, particularly preferably by snap-fit. Thus, the indicator device may be directly attached to the inner part, or indirectly via the retaining part.

According to another aspect of the present disclosure, a part of the indicator device, such as a bearing portion or an indicator housing, is formed by another structural component of the nebulizer and/or by the inner part and/or by a part thereof. Thus, a simplified construction and/or a reduction of parts can be achieved. In particular, a more cost-effective nebulizer and/or a simple assembly can be realized.

According to another aspect of the present disclosure, which can also be implemented independently, the nebulizer comprises a positioning device. By means of the positioning device, the shaft is preferably kept in a defined rotational position between two actuations and/or the positioning device is or acts as a ratchet. In this way, it is ensured that rotation of the shaft and indicator element is only performed when actuating the nebulizer. Thus, accidental rotation, in particular between two actuations, is prevented. Further, it is prevented that a user can manipulate the indicator device, e.g. by manually rotating the indicator element without actuating the nebulizer.

Preferably, by means of the positioning device, it is prevented that a drive mechanism for the shaft, in particular a gear mechanism or transmission, is or becomes (unintentionally) blocked or stuck. In particular, the shaft is held in the defined or correct position by the positioning device such that the drive mechanism can act on or rotate or index the shaft as desired. Thus, an improved and/or more secure handling is achieved, and/or the correct functioning of the indicator device is ensured.

Preferably, by means of the positioning device, it is ensured that the shaft, indicator element and/or a rider for locking the nebulizer are in the correct position. In particular, it is ensured that the correct number is indicated and/or that the nebulizer is not locked too early or too late. Thus, an improved and/or more secure handling is achieved.

Particularly preferably, the shaft is blocked from rotating backwards by means of the positioning device.

Preferably, the shaft is held in the defined rotational position by means of the positioning device, particularly preferably in an engaging and/or latching manner.

The positioning device is preferably embodied as or comprises a projection and/or flexible arm, in particular engaging with a shaft gear of the shaft. Preferably, the projection and/or flexible arm forms the ratchet.

Preferably, the positioning device is embodied, in particular as ratchet, to flex away when the shaft is rotated in one direction and/or to block a rotation of the shaft in the other direction. Preferably, In this way, the positioning device acts as ratchet and/or allows rotary motion of the shaft in only one direction while preventing motion in the opposite direction.

Particularly preferably, the positioning device is integrally formed with or formed by the inner part and/or the part of the nebulizer comprising the shaft or forming a bearing for the shaft.

It is preferred that the nebulizer comprises an energy store, such as a drive spring. The energy store can be loaded, preferably by manual actuation of the nebulizer. In this way, energy is stored which can be used for the subsequent nebulization of a dose of fluid. For example, energy can be stored in a drive spring by tensioning, in particular compressing, said spring. Relaxation of the spring, thus releasing the stored energy, can be used to force a dose of fluid out of the nebulizer.

Loading of the energy store, in particular tensioning/compressing of the drive spring, is preferably performed by relative rotation of the inner part, preferably together with the lower housing part, relative to an upper housing part of the nebulizer. This relative rotation is preferably used to drive the shaft and, thus, the indicator element.

Actuation of the nebulizer, in particular loading the energy store, preferably causes a rotation of the shaft and in particular of the indicator element rotatably coupled to the shaft. For this purpose, the nebulizer preferably comprises one or more drive portions which cooperate or mesh with the shaft or a shaft gear thereof when the nebulizer is actuated. In particular, the one or more drive portions are arranged such that the shaft is rotated by a defined angle. In this way, a precise movement of the shaft and the indicator element is ensured which enables a precise indication or counting and thus an easy and secure handling.

The one or more drive portions are preferably formed by one or more protrusions of the part rotating relative to the shaft, in particular the upper housing part, the shaft preferably being attached to the inner part. This allows for a very simple construction.

The nebulizer or inner part preferably comprises the retaining part for retaining, bearing or biasing the energy store. In particular, the retaining part forms a bearing for an axial end of the energy store.

Particularly preferably, the indicator device is attached to the retaining part and/or the retaining part forms part of the indicator device. This allows for a very compact and/or simple construction and/or assembly.

Particularly preferably, the retaining part retains both the energy store and the indicator device.

Preferably, the retaining part forms or provides a bearing for the rotation of the indicator element.

The indicator device preferably comprises an indicator housing, with the indicator element being accommodated inside the indicator housing. The indicator housing is preferably fixed to the inner part or the retaining part, in particular at an axial or free end or from below. This allows for a compact and/or robust construction in which the indicator housing is non-detachably fixed to the inner part or retaining part and the indicator element is rotatably accommodated or held within the indicator housing.

The indicator element preferably comprises or forms an indicator gear or a toothing. Preferably, the nebulizer comprises a corresponding drive gear which is attached to the shaft. In this way, a particularly easy, stable and/or compact coupling between the indicator element and the shaft is achieved. In particular, the indicator gear/toothing and the drive gear are directly coupled with each other. This is conducive to a cost-effective and/or simple construction and/or assembly of the nebulizer. In particular, no further parts for the coupling, such as an intermediate gear, are necessary.

Preferably, the toothing is on the outer circumference of the indicator element and/or the shaft or its drive gear engages the indicator element or its toothing from the outside. This has the advantage that the inside of the indicator element is free or that no space for the shaft or drive gear is required in said inside. Advantageously, there is more space available for other parts of the nebulizer and/or a container holding the fluid.

Particularly preferably, the indicator element is embodied as or forms a spur gear and/or toothed wheel.

When assembling the nebulizer, the shaft is preferably inserted into a bearing lug of the nebulizer or inner part and the drive gear is attached to, in particular plugged or clipped onto, the shaft from the opposite side and/or the face end extending through the lug. This allows a simple and/or robust construction. In this way, the shaft is preferably held in an axially and/or radially fixed position.

Preferably, in addition to the indicator device or indicator element, the shaft drives an optional second indicator device and/or a lock or locking device of the nebulizer.

Preferably, the lock or locking device is actuated when a predetermined number of actuations or discharged doses has been reached or exceeded. Preferably, the lock or locking device cannot be reset such that the nebulizer is in a permanently locked state in which no further use is possible. This allows for a secure handling of the nebulizer.

Particularly preferably, the lock or locking device is realized by means of a locking spring, for example as disclosed in WO 2004/024340 A1.

The shaft preferably comprises a threaded portion with an associated rider. Rotation of the shaft preferably linearly drives the rider along the threaded portion.

Particularly preferably, the rider actuates the lock or locking device of the nebulizer, in particular when reaching its uppermost or end position.

In addition or alternatively, the rider may form or may be used as second indicator device, wherein the height of the rider indicates the number of actuations performed or still possible. However, both indicator devices show essentially the same information in this case, wherein the indication of the first indicator device can be made more precise. It is therefore preferred to use or provide only one, namely the first, indicator device as described above.

All aspects of the present disclosure mentioned above and in the following can be realized independently of one another and in any combination. Further advantages, features, aspects and characteristics of the present invention will become apparent from the claims and the following description of a preferred embodiment with reference to the drawings.

DETAILED DESCRIPTION

In the figures the same reference numbers are used for identical or similar parts, preferably resulting in corresponding or comparable properties and advantages, even if the associated description is not repeated.

Figure 1:
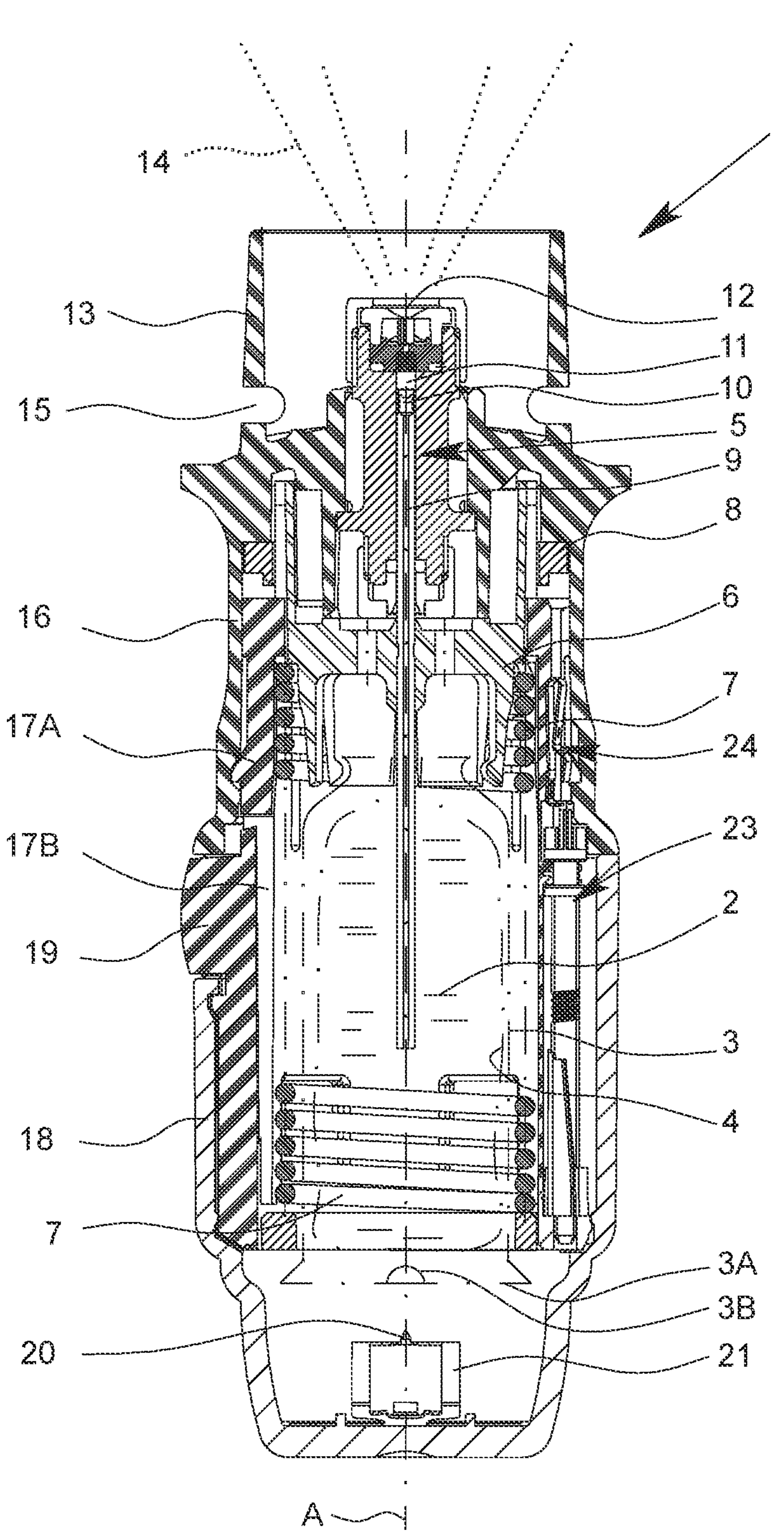
FIG. 1 is a schematic section of a known system/nebulizer in a non-tensioned state.
Figure 2:
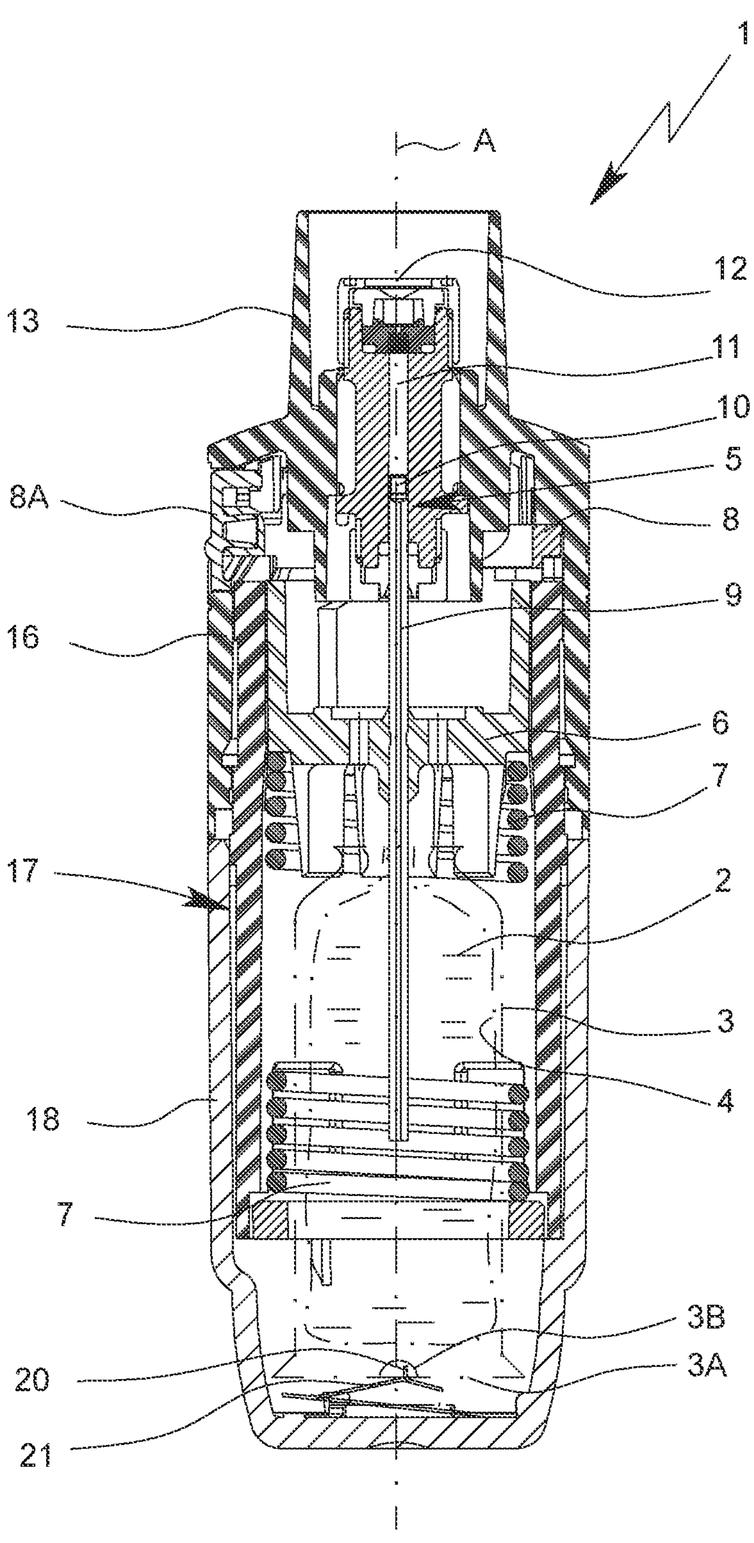
FIG. 2 is a schematic section of the known system/nebulizer according to FIG. 1, but in a tensioned state.

FIG. 1 and FIG. 2 show a known system/dispensing device/nebulizer 1 for atomizing, nebulizing and/or dispensing a fluid 2, in particular a pharmaceutical composition, a medicament or the like, schematically shown in a non-tensioned, initial and/or unloaded state (FIG. 1) and in a tensioned, ready-to-use, activated and/or loaded state (FIG. 2).

The system/nebulizer 1 is preferably adapted to dispense or nebulize the fluid 2 or a dose thereof, in particular in form of an aerosol 14 (as indicated by dotted lines in FIG. 1).

Preferably, the nebulized/dispensed fluid 2 or aerosol 14 can be breathed in or inhaled by a user/patient (not shown).

Usually, the dispensing/inhaling is done at least once a day, preferably several times a day, in particular at set intervals, depending on the complaint/illness from which a patient is suffering.

The system/nebulizer 1 is preferably constructed as a portable inhaler and/or operates preferably only mechanically and/or without any propellant/gas. Nevertheless, other constructions are possible as well.

The system preferably comprises the nebulizer 1 and a container 3 containing the fluid 2. With other words, the nebulizer 1 and the container 3 preferably form the system.

The nebulizer 1 is preferably adapted to receive the preferably insertable or replaceable container 3, preferably axially and/or from below, as shown in FIGS. 1 and 2.

The following description does not differentiate between the system and the nebulizer 1. When in the description reference is made to nebulizer 1, this shall also encompass a system comprising the nebulizer 1 and the (inserted) container 3, unless otherwise stated.

The nebulizer 1 or container 3 preferably comprises and/or forms a reservoir 4 for the fluid 2 which is to be dispensed, in particular in nebulized or atomized form.

Preferably, the container 3 or reservoir 4 contains multiple doses of the fluid 2, in particular sufficient to provide at least 60, 100 or 150 and/or up to 200 or more dosage units or doses, i.e. to allow at least 60, 100 or 150 and/or up to 200 sprays or applications.

The (maximal) volume of the reservoir 4 preferably amounts to at least 0.5 ml or 2 ml, in particular at least 4 ml or 6 ml, and/or of at most 100 ml or 50 ml, in particular at most 20 ml or 10 ml.

The number of doses or total volume of fluid 2 contained in the container 3 or reservoir 4 can vary depending on the fluid 2 or the container 3 and/or on the necessary medication.

Preferably, the nebulizer 1 is adapted to dispense a dose of at least 1 μl or 5 μl, in particular at least 10 μl or 15 μl , and/or of at most 100 μl or 80 μl , in particular of at most 60 μl , of fluid 2 per use or actuation.

As already mentioned, it may be possible to replace or exchange the container 3. With other words, the nebulizer 1 may be reusable and/or can be used with a new container 3 once a container 3 is empty. However, also solutions are possible in which the nebulizer 1 can be used with only one container 3 and/or in which the container 3 or reservoir 4 is (unexchangeable) integrated into the nebulizer 1.

Optionally, the total number of actuations or uses of the nebulizer 1 and/or the number of containers 3 which can be used with the same nebulizer 1 is restricted, e.g. to a total number of four, five or six.

The container 3 is preferably at least essentially cylindrical and/or embodied as a hollow cylinder. Mostly preferred, the container 3 is at least essentially rotationally symmetric and/or elongated.

Preferably, the nebulizer 1 and/or container 3 comprise or define an axis A, preferably wherein the axis A is a longitudinal, central, motion and/or rotational axis of the nebulizer 1 and/or container 3. Mostly preferred, the axis A is a common axis of the nebulizer 1 and container 3.

The axis A preferably runs centrally through the nebulizer 1 and/or container 3.

In the following—if not explicitly stated otherwise—spatial descriptions are preferably made with reference to the axis A, in particular when radial and/or axial alignments or arrangements are specified. Thus, the terms "radial" or "axial" preferably relate to the axis A of the nebulizer 1 and/or container 3.

Preferably, the reservoir 4 for the fluid 2 is variable, in particular collapsible/reducible. In particular, the reservoir 4 or its volume is reduced (automatically) when and/or each time a dose of the fluid 2 is withdrawn from the container 3. In particular, the container 3 can comprise or form a variable or collapsible volume for the fluid 2, such as a (flexible) inner container of variable reservoir 4, preferably a collapsible bag. In FIGS. 1 and 2, the collapsible volume is formed by a bag. However, also other solutions are possible here, for example a movable piston within the container 3.

Optionally, the container 3, in particular its base 3A, comprises a ventilation/aeration, e.g. a valve, opening or hole 3B, for venting/aeration of the container 3, preferably in order to enable or support withdrawal of fluid 2 and/or collapse of the bag or reservoir 4.

Preferably, the ventilation opens automatically and/or before or during first use of the nebulizer 1 and/or container 3.

Preferably, the nebulizer 1 comprises a preferably mechanically operated delivery mechanism/fluid pump 5 for withdrawal, pressurizing, conveying and/or nebulizing/dispensing of the fluid 2, in particular of a—preferably preset and/or adjustable—dosage amount thereof.

The fluid pump 5 is preferably adapted to withdraw or suck fluid 2, namely a dose of the fluid 2, from/out of the container 3 or reservoir 4, preferably during a tensioning process or loading process of the nebulizer 1 and/or in a first step.

Subsequently, the withdrawn fluid 2 or dose of fluid 2 is or can be dispensed, in particular (first) pressurized and/or (then) nebulized, preferably by means of the fluid pump 5, in particular during a dispensing process or nebulizing process of the nebulizer 1 and/or in a second step.

Thus, the normal use of the nebulizer 1 preferably comprises a two-stage procedure, i.e. the loading process, in particular in which energy is transferred into an energy store 7 and/or in which a pump/pressure chamber 11 of the nebulizer 1 or fluid pump 5 is filled with fluid 2, and the dispensing process, in particular in which fluid 2 is ejected from the pump/pressure chamber 11.

Preferably, the mechanical energy that has been stored during the loading process is released during the dispensing process in order to pressurize and/or nebulize the withdrawn fluid 2 or a dose thereof.

Preferably, the nebulizer 1 comprises an energy store 7. In the present embodiment, the energy store 7 is embodied as a drive spring, in particular a spiral spring, preferably wherein the drive spring is at least partially arranged around and/or encompasses the container 3.

The energy store 7 is preferably loaded during the loading process. In case the energy store 7 is embodied as a drive spring, the drive spring is preferably tensioned/compressed during the loading process, in which case the loading process is also referred to as tensioning process. The energy stored in this way is preferably released during the subsequent dispensing process and/or for dispensing or nebulizing the fluid 2 or a dose thereof.

As already mentioned, the nebulizer 1 is preferably adapted to (axially) receive the container 3, mostly preferred in order to establish a fluid connection between the container 3, in particular its reservoir 4, and the fluid pump 5.

Preferably, the nebulizer 1 comprises a holder 6 for—in particular releasably and/or axially—holding the container 3 and/or in order to establish a mechanical connection between the container 3 and the nebulizer 1.

Preferably, the energy store 7 is associated to and/or (axially) abuts the holder 6. Preferably, the holder 6 is (axially) moved to load the energy store 7 and/or tension the drive spring.

The holder 6 and the fluid pump 5 are preferably mechanically connected to one another. In this way, the energy of the energy store 7 is transferred from the energy store 7 via the holder 6 to the fluid pump 5.

The nebulizer 1 preferably comprises a blocking element 8, preferably wherein the blocking element 8 is adapted to catch and/or block the holder 6 and/or energy store 7 after the loading process is completed and/or in such a way that the energy stored during the earlier loading process is not unintentionally and/or immediately released.

Preferably, the blocking element 8 is manually actuated, in particular by pressing a release button 8A of the nebulizer 1 or blocking element 8, in order to release the holder 6 and/or the energy store 7, preferably allowing the energy store 7 to release energy, in particular allowing the compressed drive spring forming the energy store 7 to expand. With other words, the dispensing process is preferably initiated by manually actuating the blocking element 8, in particular the release button 8A.

The nebulizer 1, in particular the fluid pump 5, preferably comprises a conveying/connecting element 9 (e.g. a conveying tube), a non-return valve 10, a pressure chamber 11, a nozzle 12 and/or a mouthpiece 13.

Preferably, the connecting element 9 fluidically connects the container 3, in particular its reservoir 4, to the nebulizer 1, in particular the fluid pump 5, when inserting the container 3 into the nebulizer 1.

Thus, by inserting the container 3 into the nebulizer 1, the container 3 is—preferably simultaneously—mechanically connected to the nebulizer 1, in particular by means of the holder 6, and fluidically connected to the nebulizer 1, preferably its fluid pump 5, in particular by means of the connecting element 9.

The connecting element 9 preferably penetrates and/or pierces the container 3, in particular the reservoir 4, when inserting the container 3 into the nebulizer 1 and/or connecting the container 3 to the fluid pump 5.

Preferably, the connecting element 9 is constructed as an elongated hollow cylinder and/or as a preferably capillary tube. Mostly preferred, the connecting element 9 is at least essentially coaxial to the axis A.

Preferably, the connecting element 9 is rigid, in particular made out of metal, mostly preferred out of stainless steel, and/or adapted to pierce or break the container 3 and/or a closure/seal/cover thereof.

Preferably, the connecting element 9 is constructed as a capillary, in particular having an inner diameter of less than 1 mm or 0.8 mm, mostly preferred less than 0.7 mm or 0.5 mm, and/or more than 0.1 mm or 0.2 mm. However, the inner diameter should not be dimensioned to small as this reduces the flow rate that can be achieved within the connecting element 9.

When the energy store 7 is loaded in the loading process, the container 3, the holder 6, the connecting element 9 and/or the non-return valve 10 are preferably moved (together) downwards and/or towards the base/bottom of the nebulizer 1.

Due to the movement of the container 3, the holder 6, the connecting element 9 and/or the non-return valve 10, the volume of the pressure chamber 11 is preferably enlarged and/or the pressure within the pressure chamber 11 is decreased, in particular such that the fluid 2 is withdrawn from or sucked out of the container 3 via the connecting element 9 into the fluid pump 5, in particular through the non-return valve 10 into the pressure chamber 11.

In this state and/or at the end of the loading process, the holder 6 or energy store 7 is caught by the blocking element 8 so that the energy is kept in the energy store 7, in particular so that the drive spring is kept tensioned/compressed, as already mentioned. Subsequently, the nebulizer 1 is in the loaded/tensioned/ready-to-use/activated state.

In the context of the present disclosure, loading of the energy store 7 is preferably to be understood as (further) compressing the drive spring forming the energy store 7. Thus, energy is preferably stored in the loaded energy store 7. The activated, tensioned, and/or loaded state of the nebulizer 1 is preferably a state in which the drive spring is (further) compressed with respect to its unloaded, non-tensioned, and/or initial state and/or in which the nebulizer 1 can be actuated and/or a dose of the fluid 2 can be dispensed.

The unloaded, non-tensioned and/or initial state of the nebulizer 1 is preferably the state in which the drive spring is relaxed or less compressed compared to the loaded, tensioned and/or activated state. Mostly preferred, the unloaded, non-tensioned, and/or initial state is the state (immediately) after actuation of the nebulizer 1 and/or after dispensing a dose of the fluid 2.

Preferably, the energy stored in the energy store 7 is released by (partial) expansion of the drive spring from the compressed/tensioned state into the initial/non-tensioned state. However, also other solutions are possible, for example in which loading of the energy store 7, in particular tensioning of the drive spring, is to be understood as (further) expanding the drive spring with respect to its non-tensioned/initial state and the energy stored in the drive spring is released by (partial) contraction of the drive spring.

During the dispensing process, i.e. after actuating/pressing the blocking element 8, the container 3, the holder 6, the connecting element 9 and/or the (now closed) non-return valve 10 are/is preferably moved (together) towards and/or relatively to the nozzle 12 and/or mouthpiece 13 and/or away from the base/bottom of the nebulizer 1, in FIGS. 1 and 2 upwards, thereby decreasing the volume of the pressure chamber 11.

Due to the now closed non-return valve 10, the fluid 2 or a dose thereof in the pressure chamber 11 is pressurized. Thus, during the dispensing process the non-return valve 10 preferably acts as a ram or piston.

The pressure generated in this way causes the fluid 2 or a dose thereof to flow through the nozzle 12, whereupon it is nebulized/dispensed, preferably in form of the aerosol 14, as indicated by dotted lines in FIG. 1.

Generally, the nebulizer 1 operates with a spring and/or fluid pressure (in the pressure chamber 11) of at least 5 MPa or 10 MPa, in particular of at least 20 MPa, and/or of at most 200 MPa or 150 MPa, mostly preferred of at least essentially 30 MPa.

The fluid 2 is converted into or nebulized as an aerosol 14, the droplets thereof having an aerodynamic diameter of up to 20 μl , preferably of at least 3 μl and/or of at most 10 μl.

The generated jet spray is preferably cone-shaped and/or has an opening angle of at least 20°, preferably at least 60° or 80°, and/or of at most 160°, in particular of at most 120° or 100°.

A user/patient (not shown) can inhale the aerosol 14 generated in this way, preferably while air can be sucked into the mouthpiece 13 through at least one optional air supply opening 15 in the mouthpiece 13.

Preferably, the aerosol 14 is dispensed at the top of the nebulizer 1 and/or in a direction of the axis A, in FIGS. 1 and 2 upwards.

When normally operated, the axis A of the nebulizer 1 or container 3 is preferably aligned at least essentially vertically. However, it is also possible to use/hold the nebulizer 1 in any other position during the loading process and/or dispensing process.

Preferably, spatial expressions such as "top", "bottom", "above" and "below", "upper" and "lower" refer to said preferred usage orientation in which the axis A is aligned at least essentially vertically and the aerosol 14 is dispensed at the top/upwards. These spatial expressions also correspond to the orientations depicted in the figures.

The nebulizer 1 preferably comprises an upper housing part 16, an intermediate/inner part 17 and/or a lower housing part 18, preferably wherein the parts 16, 17 and 18 are separate components. Preferably, the upper housing part 16 and lower housing part 18 form a housing of the nebulizer 1.

The inner part 17 preferably comprises an upper inner part 17A and a lower inner part 17B. The upper and lower inner part 17A, 17B are preferably formed together as one piece.

The inner part 17 is preferably at least essentially cylindrical, in particular formed as a hollow cylinder. The axis A of the nebulizer 1 preferably coincides with or is the symmetry axis/cylinder axis of the inner part 17.

The upper housing part 16 and the lower housing part 18 each preferably comprises or forms an axial end of the preferably elongated nebulizer 1. Preferably, the intermediate/inner part 17 is arranged between and/or mechanically connects the upper housing part 16 and the lower housing part 18. In particular, the upper inner part 17A is connected with the upper housing part 16 and the lower inner part 17B is connected with the lower housing part 18.

The upper housing part 16 preferably comprises or forms the mouthpiece 13, whereas the lower housing part 18 preferably comprises or forms a bottom/base of the nebulizer 1.

The inner part 17 and/or lower housing part 18 are/is movable, preferably rotatable, relative to the upper housing part 16 and/or the mouthpiece 13. In particular, the lower housing part 18 is manually rotatable and/or releasably fixed/fitted/held onto the inner part 17, preferably by means of a retaining element 19.

In order to insert and/or replace the container 3, the nebulizer 1, in particular the lower housing part 18, can be opened and/or the lower housing part 18 can be detached from the nebulizer 1, in particular its inner part 17.

The lower housing part 18 is preferably cap-like and/or fits around or over a bottom of the container 3. Mostly preferred, the nebulizer 1, in particular its upper housing part 16, lower housing part 18 and/or inner part 17, encompasses the container 3 completely, i.e. axially and radially. However, other solutions are possible as well, e.g. wherein the container 3 axially protrudes out of the nebulizer 1.

As already mentioned, the nebulizer 1 or energy store 7 is preferably manually tensioned/loaded, in particular by actuation/rotation of an actuation member, preferably by rotation of the lower housing part 18 or any other component relative to the upper housing part 16, preferably carrying with it or driving the inner part 17.

The inner part 17 preferably acts on a gear/transmission (not shown) to transform the rotation into an axial movement of the container 3, holder 6 and/or connecting element 9. As a result, the energy store 7 is loaded, in particular the drive spring is tensioned, in the axial direction by means of the gear/transmission formed between the inner part 17 and the holder 6.

During the loading process, the container 3, holder 6 and/or connecting element 9 are/is moved axially away from the nozzle 12 and/or mouthpiece 13 and/or towards the bottom of the nebulizer 1 until the container 3, holder 6 and/or connecting element 9 occupies/assumes a lower position, as shown in FIG. 2. In this activated/tensioned/loaded state of the nebulizer 1 and/or when the container 3 is in the lower position, the energy store 7 is loaded, in particular the drive spring is under tension, and caught or held by the blocking element 8, as already mentioned.

During the subsequent dispensing process, which is preferably initiated by actuating or releasing the blocking element 8, e.g. by pressing the release button 8A, the container 3, holder 6 and/or connecting element 9 are/is moved back into its original/initial/upper position, as shown in FIG. 1, in particular by (the force of) the energy store 7.

Thus, the container 3, holder 6 and/or connecting element 9 execute/executes a lifting or stroke movement during the loading and dispensing process, preferably along the (motion) axis A.

An aeration/ventilation means, such as a piercing element 20 arranged in the nebulizer 1 or its housing, in particular the lower housing part 18, preferably opens a ventilation/aeration or venting hole 3B of the container 3 and/or pierces the container 3, in particular a cover, foil or seal at the base 3A of the container 3, when the container 3 makes contact with it for the first time. In this way, air can flow into the container 3 and pressure compensation can take place when fluid 2 is withdrawn from the container 3 during the loading of the nebulizer 1. Preferably, the piercing element 20 is arranged at an axially acting spring 21 which abuts the base 3A of the container 3 when first loading or tensioning the nebulizer 1, in particular due to the lifting/stroke movement of the container 3.

Figure 3:
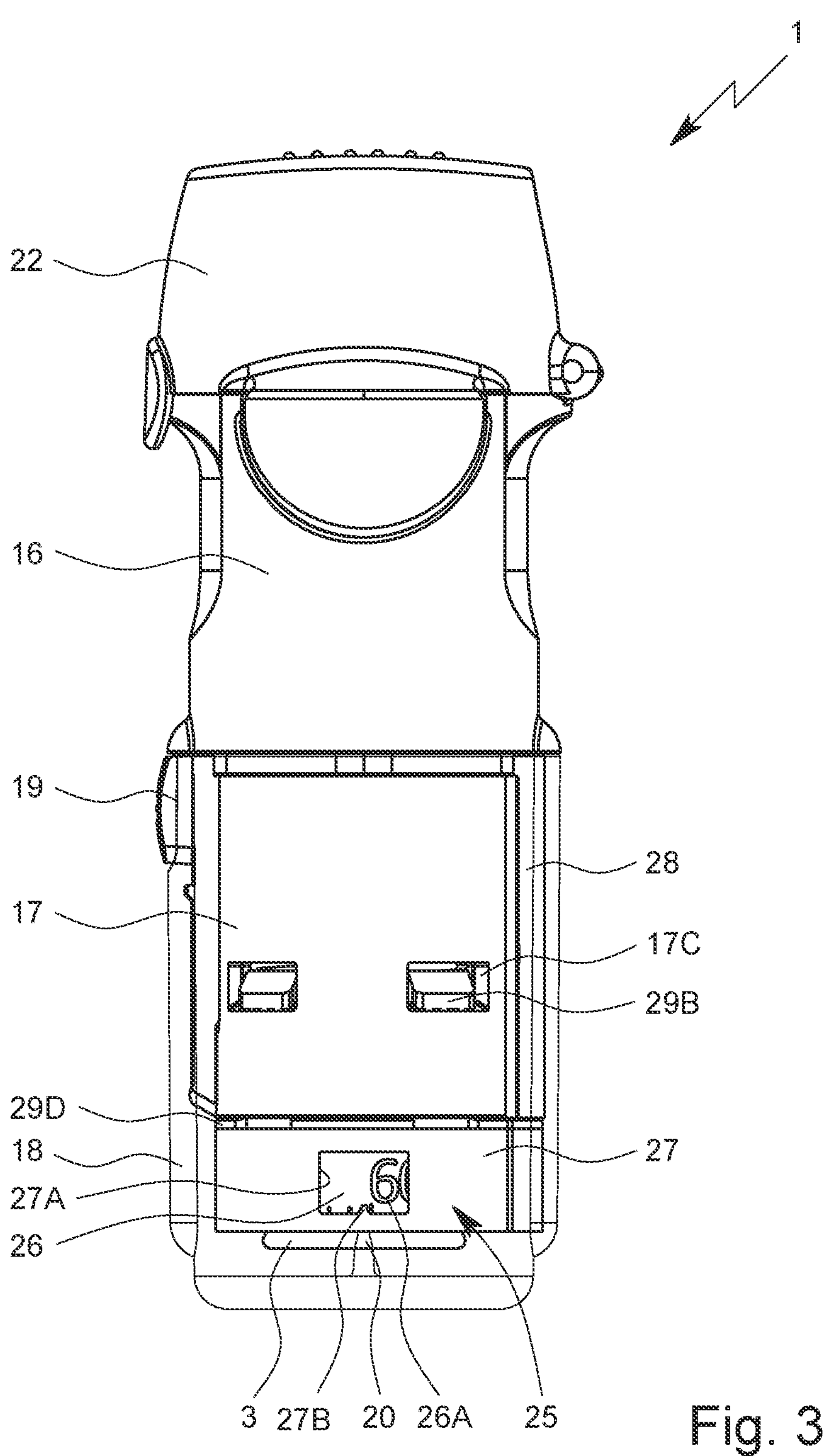
FIG. 3 is a schematic front view of the proposed system/nebulizer.
Figure 4:
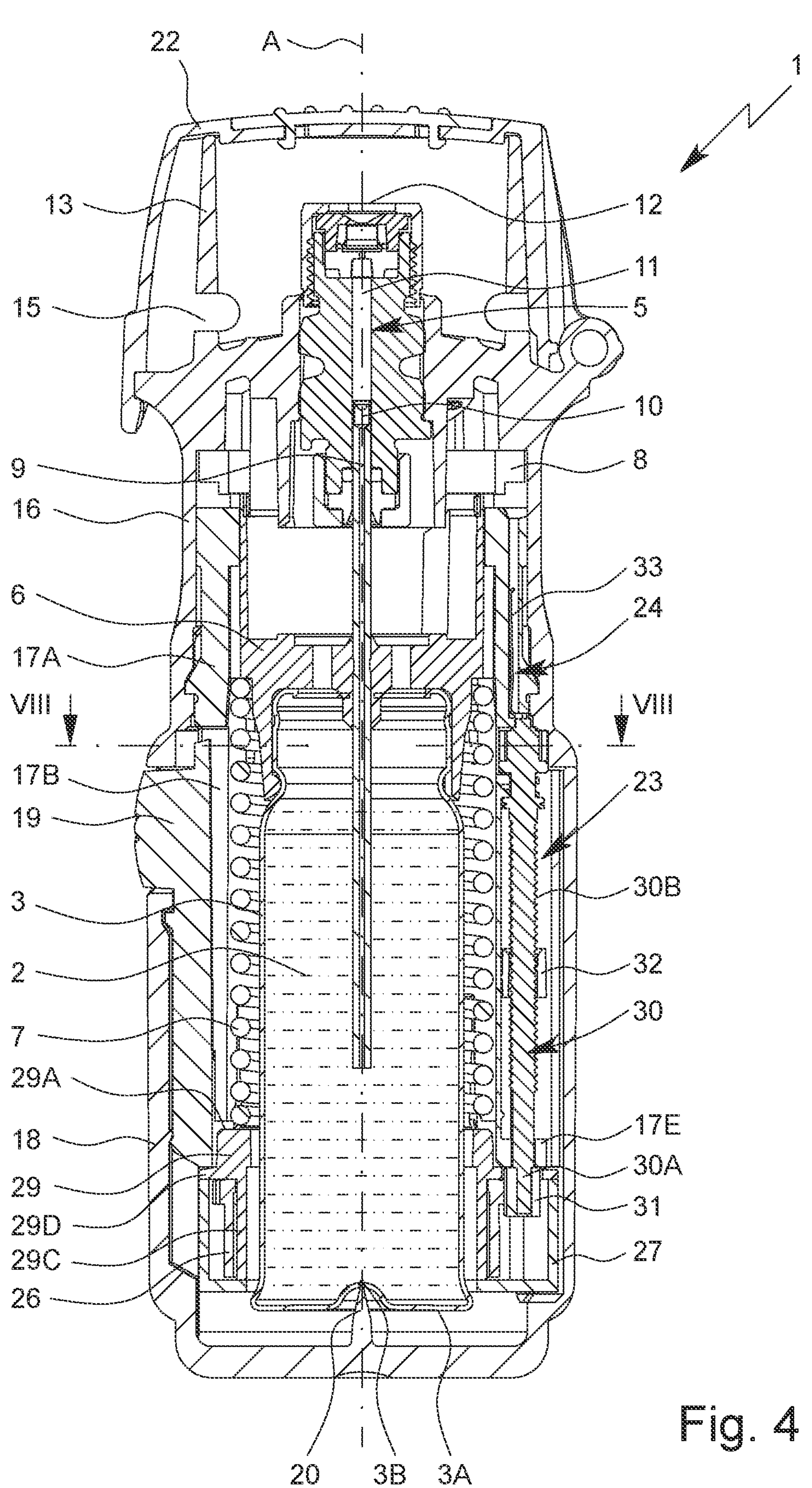
FIG. 4 is a schematic section of the system/nebulizer according to FIG. 3.
Figure 6:
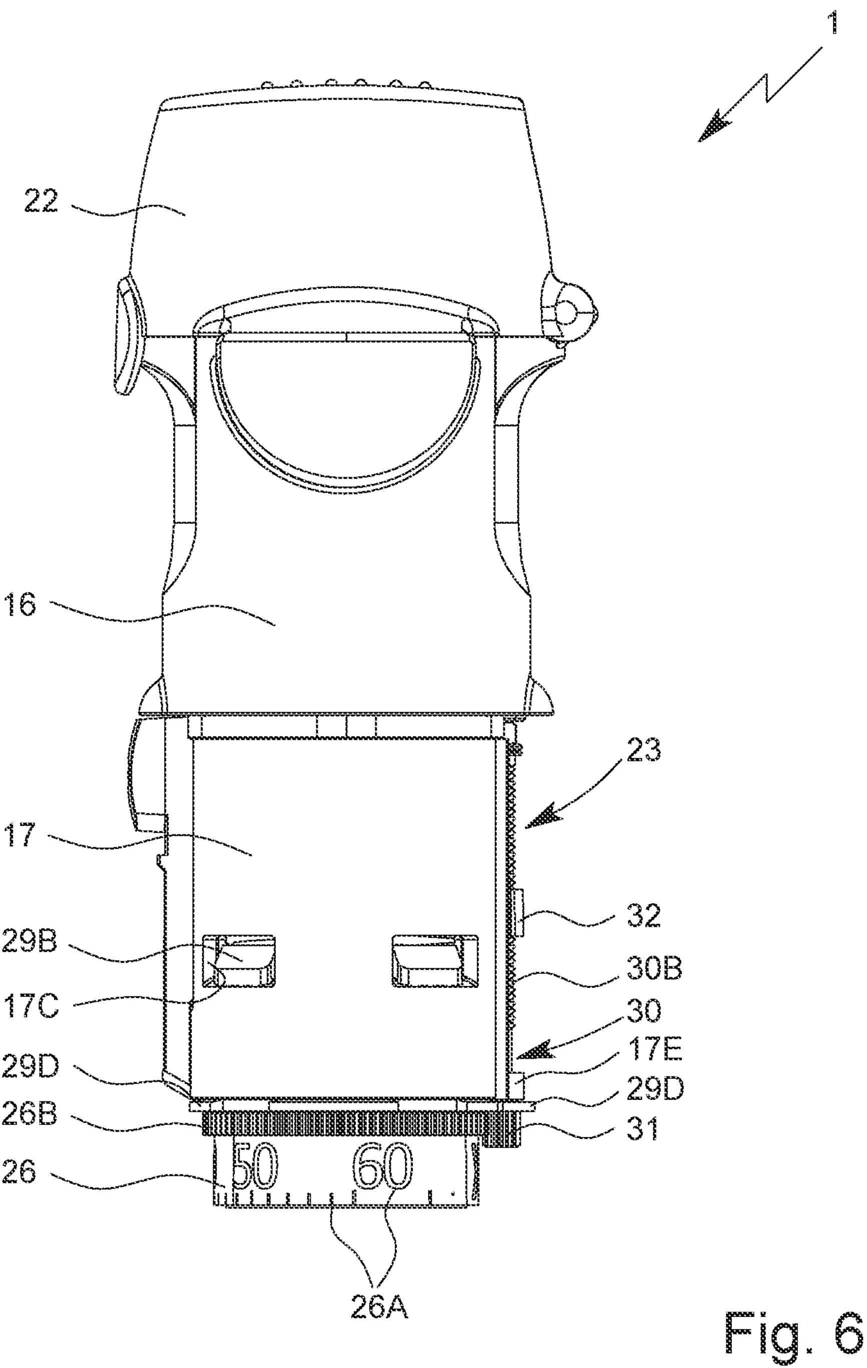
FIG. 6 is a schematic view similar to FIG. 3, but with certain parts of the system/nebulizer being removed.

Preferably, the nebulizer 1 or its mouthpiece 13 can be closed by an optional mouthpiece cover 22 in the unloaded/non-tensioned state, as shown in FIGS. 3, 4 and 6. The mouthpiece cover 22 is preferably pivotable to allow opening of the mouthpiece 13 for using the nebulizer 1.

Preferably, the nebulizer 1 comprises a locking device 24 which locks the nebulizer 1 against (further) actuation or use, in particular blocks further rotation of the housing part 18/inner part 17 and, thus, loading of the nebulizer 1 or its energy store 7 (embodiments are shown in the figures) or (in alternative or in addition) blocks actuation of the blocking element 8 (not shown in the embodiments depicted in the figures), in a locked state when a certain number of actuations or operations or discharged doses has been reached or exceeded.

Preferably, the nebulizer 1 comprises a drive device 23 for driving or actuating the locking device 24 and/or an indicator device 25.

In the following and with reference to FIGS. 3 to 8, a preferred embodiment of the nebulizer 1 according to the disclosure is described and shown, wherein primarily important aspects and differences will be described and the previous aspects, features and explanations apply preferably additionally or correspondingly even without repetition.

Figure 5:
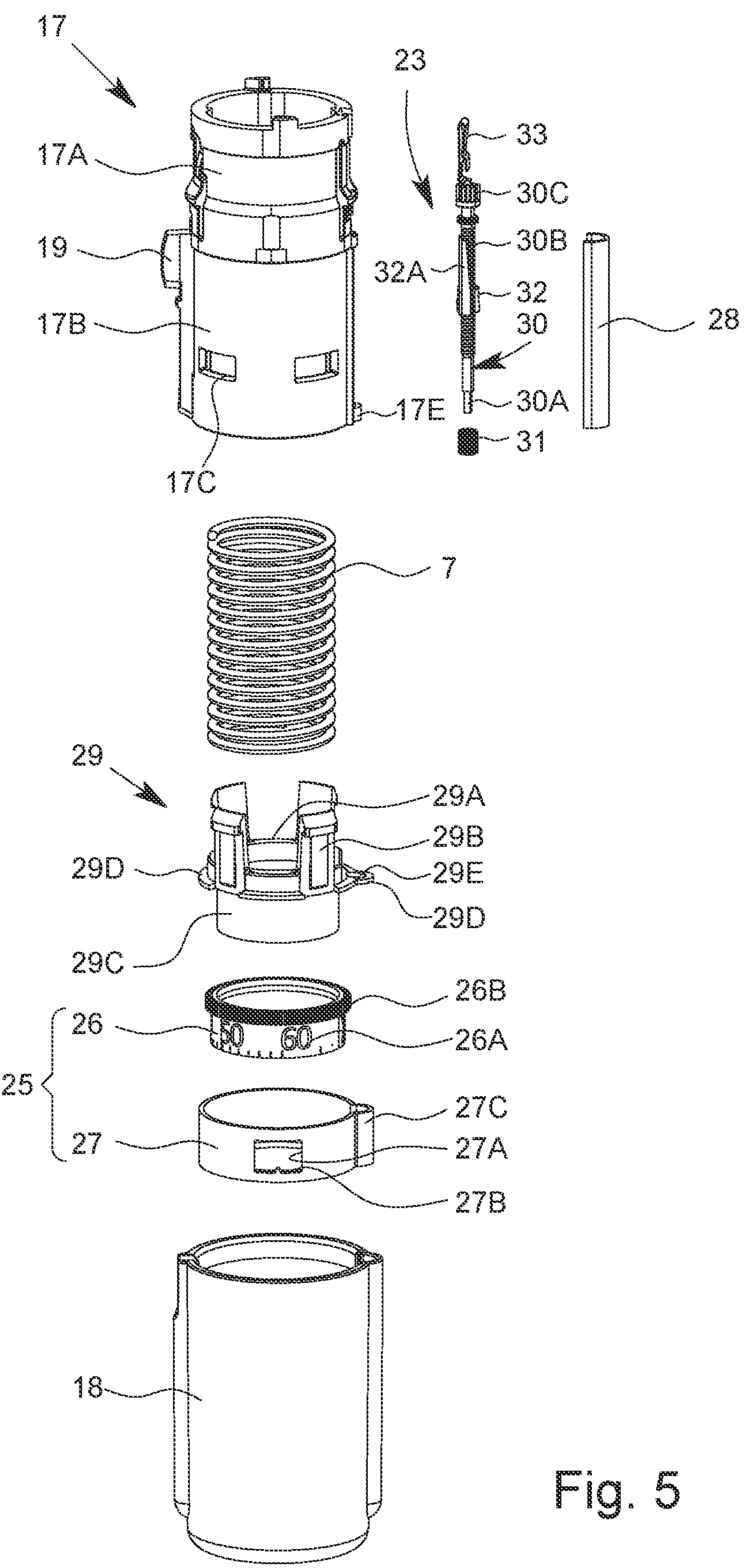
FIG. 5 is a schematic exploded view of parts of the system/nebulizer according to FIG. 3.

FIG. 3 shows a schematic front view of the proposed nebulizer 1 when fully assembled with inserted container 3 and in the loaded/tensioned state. FIG. 4 shows a schematic section of the nebulizer according to FIG. 3. FIG. 5 shows a schematic exploded view of certain parts of the nebulizer 1, including the inner part 17, drive device 23, energy store 7, indicator device 25 and lower housing part 18.

The nebulizer 1 according to the disclosure comprises preferably the indicator device 25.

The indicator device 25 preferably counts and/or indicates the actuations or operations of the nebulizer 1 or the doses of fluid 2 already discharged or still possible to discharge. In particular, the indicator device 25 is for counting and/or indicating a number of actuations or uses performed or still possible with the nebulizer 1 and/or container 3.

In the sense of the present disclosure, an actuation (use or operation) of the nebulizer 1 is preferably to be understood as the process performed by a user in order to nebulize or discharge one dose of fluid 2, in particular for inhalation by the user, or to tension or load the nebulizer 1 for nebulization or discharge of one dose of fluid 2.

As already explained above, each actuation (or use) preferably comprises a two-stage procedure. In a first step—the loading process or tensioning process—energy is transferred into the energy store 7 and/or the pump chamber 11 is filled with fluid 2. In a second step—the dispensing process or nebulizing process—the stored energy is released and/or fluid 2 is ejected from the pump chamber 11, causing a dose of fluid 2 to be dispensed/discharged/nebulized. Both steps or processes are preferably separately or sequentially initiated, in particular manually, by a user or patient.

Preferably, the loading process and the dispensing process are performed shortly after each other by a user/patient. Therefore, it is sufficient for the indicator device 25 to indicate or count the loading process or loading of the energy store 7 as an actuation. Alternatively or in addition, the dispensing process or releasing of the energy from the energy store 7 may be detected or registered by the indicator device 25 as an actuation.

Particularly preferably, actuation of the nebulizer 1 is or comprises rotating the inner part 17, in particular around its symmetry axis and/or relative to the upper part 16. Such rotation may be a partial rotation, e. g. by about 180°, or a full rotation.

It is noted that the indicator device 25 does not necessarily need to count or indicate every actuation of the nebulizer 1 and/or could just indicate or count actuations in lots of more than one actuation, for example in lots of two or five actuations. However, the indicator device 25 preferably indicates or counts in lots of a small number, in particular of at most five or ten actuations.

When using the nebulizer 1 for the first time, it may be that the nebulizer 1 needs to be actuated a couple of times, in particular that the energy store 7 needs to be loaded and released a couple of times, for example two to three times, before a full dose of fluid 2 can be nebulized/discharged. The need to actuate the nebulizer 1 a couple of times before it is operational is referred to as priming.

Priming is in particular necessary because the delivery mechanism and/or fluid pump 5 of the nebulizer 1, in particular the pressure chamber 11 and/or connecting element 9, are initially empty and/or filled with air, i.e. not filled with fluid 2. In this case, an actuation of the nebulizer 1 may only cause filling of or displacing air from the delivery mechanism/fluid pump 5 with fluid 2. In other words, fluid 2 sucked out of or withdrawn from the container 3 is used for filling the fluid pump 5 with fluid 2 such that not a full dose of fluid 2 or even no fluid 2 at all is dispensed or nebulized. Once the delivery mechanism/fluid pump 5 is fully filled with fluid 2, normal use/operation of the nebulizer 1, in particular nebulization of (full) doses of fluid 2, is possible.

The nebulizer 1 is preferably constructed such that priming is minimized, for example that the nebulizer 1 is operational for nebulizing after two or three initial actuations. In particular, the nebulizer 1 is constructed such that no further priming but the initial priming is necessary. It is also possible to construct the nebulizer 1 such that priming is entirely avoided, e.g. by pressurizing the container 3.

Preferably, priming of the nebulizer 1 is not counted or indicated by the indicator device 25 as a use or actuation. Instead, the indicator device 25 may be adapted to indicate that (initial) priming is necessary and/or to indicate when priming is completed.

The indicator device 25 works preferably mechanically.

Preferably, the indicator device 25 counts actuations by detecting the rotation of the inner part 17 relative to the upper housing part 16. With other words, the indicator device 25 may count the loading, in particular tensioning process, of the nebulizer 1 or its energy store 7, in particular drive spring.

Preferably, the indicator device 25 comprises an indicator element 26 and/or an indicator housing 27.

The indicator element 26 and/or indicator housing 27 are preferably formed (each) by a unitary and/or molded part.

The indicator element 26 is preferably at least essentially ring-like. Particularly preferably, the indicator element 26 forms or comprises a preferably closed ring or sleeve.

Preferably, the indicator element 26 is rotatable and/or is indexed each time an actuation is detected or counted, e.g. each time or each second time the nebulizer 1 is loaded/tensioned, the container 3 is moved, fluid 2 is drawn from the container 3, fluid 2 is nebulized, the energy store 7 pressurizes the fluid 2, or the like. Indexing means that the indicator element 26 is moved forward in increments or steps, in particular each time the nebulizer 1 is actuated or loaded or each second time the nebulizer 1 is actuated or loaded.

The rotational position of the indicator element 26 corresponds preferably to the number of actuations performed or still possible with the nebulizer 1 or container 3. In particular, said position is made visible for a user to indicate or show said number.

Preferably, the indicator element 26 comprises markings 26A, such as one or more symbols, numbers, colored or shaded areas or the like, for at least roughly indicating the number of actuations already performed or still possible with the nebulizer 1 or container 3. In particular, the indicator element 26 preferably comprises a circumferential wall or outer surface with the markings 26A.

In the embodiment shown, the indicator element 26 comprises or is provided with numbers and/or pitch lines as markings 26A. Preferably, the markings 26A, in particular the numbers and/or pitch lines, form a scale via which the number of actuations or uses performed or still possible can be read off.

Preferably, the indicator element 26 performs its indexing or rotational movement with each nebulizer actuation, in particular also already during priming. However, the markings 26A are preferably arranged such that the first few actuations, e.g. the first 4 to 6 actuations, are not counted or indicated. In this way, priming can be accounted for.

In addition, the markings 26A may comprise a first symbol or area indicating that the nebulizer 1 is not yet ready for use and/or needs to be primed, e.g. an area and/or symbol which is shown before the first number and/or pitch line, such as a distinctively colored area, a (green) triangle or the like.

Further, the markings 26A may comprise a symbol, e.g. a green point, indicating that priming has been completed, which is preferably shown (just) after the area and/or symbol that priming is necessary and/or (just) before the first number and/or pitch line. Alternatively, the first number and/or pitch line may serve as a symbol indicating that priming has been completed and/or may be distinctively colored or the like.

Further, the markings 26A may comprise a last symbol or area that indicates end of use of the nebulizer 1 or complete locking of the nebulizer 1, e.g. by an "X", a red colored area or the like. This symbol may be shown for example when the allowable number of actuations of the nebulizer 1 has been reached or exceeded, and, thus, may indicate total or final locking of the nebulizer 1, in particular by means of the locking device 24.

The indicator housing 27 preferably receives, accommodates, holds and/or covers the indicator element 26. In particular, the indicator housing 27 is at least essentially cylindrical and/or ring-like and/or is at least essentially formed similar or corresponding to the indicator element 26.

The inner diameter of the indicator housing 27 is preferably larger than or corresponds to the outer diameter of the indicator element 26.

The indicator element 26 is preferably rotatably held by the housing 27. In particular, the indicator element 26 is rotatable relative to and/or within the housing 27.

The indicator device 25 or indicator housing 27 preferably comprises a window 27A through which the relevant marking 26A, in particular the number and/or pitch line that corresponds to the number of actuations performed or still possible with the nebulizer 1 or container 3, is visible for a user/patient, preferably through the housing part 18 which is in particular transparent.

Preferably, the indicator housing 27 comprises or forms a pointer 27B, for example a protrusion in the window 27A, which points to or indicates the relevant marking 26A, in particular the number and/or pitch line that corresponds to the number of actuations performed or still possible with the nebulizer 1 or container 3.

The lower housing part 18 is preferably transparent such that the indicator device 25, in particular the indicator element 26 or the relevant marking 26A, is visible when the nebulizer 1 is closed, in particular when the lower housing part 18 is attached to the upper housing part 16 or inner part 17. However, also other solutions are possible such as the lower housing part 18 having a window or a recess through which the indicator device 25 is visible.

The nebulizer 1 can optionally comprise a drive device cover 28 as shown in FIGS. 3 and 5. The drive device cover 28 preferably covers the drive device 23, in particular a shaft 30 of the drive device 23, for protection and/or such that the drive device 23 is not visible in the assembled state. However, also other solutions are possible here. For example, the lower housing part 18 could be non-transparent in the region of the drive device 23.

In another embodiment (not shown), the drive device 23 may form a second indicator device as explained in more detail below. In this case, it may be desired that the drive device 23 or parts thereof remain visible. Accordingly, the drive device cover 28 may be transparent or may be omitted.

The indicator device 25 is preferably located at or attached to the inner part 17, in particular its lower part 17B.

Particularly preferably, the indicator device 25 is located at or attached to a free or axial end of the in particular cylinder-like inner part 17, in particular to the lower free or axial end of the inner part 17, i.e. the end which is received or accommodated in the lower housing part 18 when the nebulizer 1 is closed or fully assembled.

The indicator device 25 is preferably located at or attached to the inner part 17 such that the symmetry axis of the in particular cylinder-like or ring-like indicator device 25, in particular of its indicator element 26 and/or indicator housing 27, coincides with the axis A of the nebulizer 1 or inner part 17. Preferably, the indicator element 26 and indicator housing 27 are arranged concentrically.

Particularly preferably, the indicator device 25 is directly and/or non-detachably attached to the inner part 17, in particular its (lower) free or axial end. For example, the indicator device 25, in particular the housing 27, may be glued or welded, particularly preferably by hot pressing, ultrasonic forming or ultrasonic welding, to the inner part 17, in particular its (lower) axial or free end.

In particular, the indicator device 25 is (permanently) fixed to the nebulizer 1 or inner part 17 and/or cannot be removed from the nebulizer 1 or inner part 17 and/or cannot be replaced or exchanged.

When the nebulizer 1 is closed or fully assembled, the indicator device 25 is preferably received or accommodated within the lower housing part 18. However, the indicator device 25 is preferably embodied separate or independent from the lower housing part 18 and/or is only connected indirectly via the inner part 17 to the lower housing part 18. In particular, the indicator device 25 remains at the nebulizer 1 or inner part 17 when the nebulizer 1 is opened or the lower housing part 18 is detached/removed.

The indicator device 25 or indicator housing 27 is preferably stationary or non-movable or rotatably fixed with respect to the inner part 17 and/or lower housing part 18.

The indicator element 26 is preferably movable, in particular rotatable, with respect to the inner part 17, lower housing part 18 and/or indicator housing 27. Particularly preferably, the indicator element 26 is rotatable around the (common) axis A of the nebulizer 1, inner part 17, lower housing part 18 and/or indicator device 25.

The indicator device 25 is particularly preferably located at or attached to a retaining part 29 of the nebulizer 1 or inner part 17. Particularly preferably, the indicator device 25 is non-detachably attached to the retaining part 29.

The retaining part 29 is preferably arranged at the inner part 17 or forms part of the inner part 17.

The retaining part 29 is preferably connected to the (lower) axial or free end of the inner part 17 or its lower part 17B, particularly preferably by snap-fit, in order to hold, bear or support an end (the lower end) of the energy store 7, in particular drive spring.

The retaining part 29 preferably retains, bears or biases the energy store 7.

A preferred construction of the retaining part 29 is shown in FIG. 5. The retaining part 29 is preferably ring-like or formed as a ring. In particular, the retaining part 29 comprises or forms a preferably ring-shaped bearing surface 29A for the energy store 7, in particular drive spring.

The retaining part 29 is preferably provided with hooks or arms 29B which in particular protrude from the bearing surface 29A in the axial direction or upwards.

In the embodiment shown, the retaining part 29 preferably comprises a plurality of, here four, arms 29B distributed around the circumference of the retaining part 29 or bearing surface 29A.

The arms 29B are preferably provided for interconnection with the inner part 17.

The inner part 17, in particular its lower part 17B, preferably comprises corresponding recesses 17C for interconnection with the arms 29B of the retaining part 29, in the example shown four recesses 17C.

Preferably, the arms 29B can engage with or hook into the recesses 17C in order to form a form-fit and/or force-fit and/or snap-fit connection between the retaining part 29 and the inner part 17 or lower part 17B. The arms 29B are preferably (partly) flexible to facilitate the form-fit and/or snap-fit connection.

When assembling the nebulizer 1, the energy store 7 or drive spring is preferably inserted into the inner part 17, in particular from below, and then the retaining part 29 is pushed with its bearing surface 29A against the lower or free end of the energy store 7 until the connection between the retaining part 29 and inner part 17 or lower part 17B is established, in particular by form-fit and/or snap-fit engagement of the arms 29B and recesses 17C.

The drive spring is preferably held in the inner part 17 biased or pre-tensioned or partly compressed, in particular by means of the retaining part 29, particularly preferably also in the non-loaded or non-tensioned state of the nebulizer 1.

When loading or tensioning the nebulizer 1 or energy store 7, the drive spring is preferably further tensioned or compressed. When releasing the energy store 7, the drive spring preferably relaxes into the previous biased or pre-tensioned or pre-compressed state.

The biasing, pre-tensioning or pre-compressing is preferably provided such that the drive spring assumes a more tensioned or compressed state than this would be the case without pretension/pre-compression. In this way, a higher force when relaxing is achieved which enables a better nebulization of the fluid 2.

Preferably, it is impossible to manually disconnect or disengage the retaining part 29, in particular the arms 29B, from the inner part 17 or lower part 17B, in particular the recesses 17C.

In particular, the retaining part 29 is non-detachably attached or connected to the inner part 17 or lower part 17B, preferably by snap-fit connection, in particular by the arms 29B engaging the recesses 17C. Detaching the retaining part 29 from the inner part 17 or lower part 17B or release of the snap-fit connection is preferably impossible without tools and/or without destroying the nebulizer 1, inner part 17 and/or retaining part 29.

Preferably, the nebulizer 1, inner part 17, indicator device 25 or retaining part 29 or a support portion 29C of the inner part 17 or retaining part 29 rotatably bears or holds the indicator element 26, preferably by axial and/or radial engagement. In particular, the retaining part 29 or the support portion 29C forms a bearing for the (rotation of the) indicator element 26.

The retaining part 29 preferably comprises the circumferential or ring-shaped support portion 29C for the indicator element 26. The indicator element 26 is preferably radially supported and/or borne by the support portion 29C and/or encompasses the retaining part 29 or its support portion 29C.

Preferably, the inner diameter of the indicator element 26 at least essentially corresponds to the outer diameter of the support portion 29C. However, the indicator element 26 is preferably rotatably borne or supported by the retaining part 29 or support portion 29C. In particular, the indicator element 26 can rotate on the retaining part 29 or support portion 29C.

The inner part 17 or retaining part 29 preferably comprises a connection portion 29D for connecting the indicator device 25 or indicator housing 27 with the inner part 17 or retaining part 29.

In the embodiment shown, the connection portion 29D is preferably formed as one or more radial protrusions or as a circumferential edge of the retaining part 29. In particular, the indicator housing 27 can be glued or welded to the connection portion 29D, particularly preferably by hot pressing, ultrasonic forming or ultrasonic welding. However, also other solutions are possible here, for example connecting the indicator device 25 by snap-fit or the like.

It is preferred that the indicator device 25 is located at or attached to the retaining part 29. However, also other solutions are possible in which the indicator device 25 is (directly) attached to other parts of the inner part 17, in particular (directly) to the lower inner part 17B, particularly preferably in a non-detachable manner. In this case, the inner part 17 may (directly) comprise one or more corresponding connecting portion(s) 29D.

Preferably, a part of the indicator device 25, such as a bearing portion or the indicator housing 27, is formed by another structural component of the nebulizer 1 and/or by the inner part 17 and/or by a part thereof, in particular by the retaining part 29 or its support portion 29C.

The container 3 is preferably located inside of the inner part 17 and/or indicator device 25. In particular, the container 3 is encompassed by the inner part 17, energy store 7, indicator device 25, indicator element 26, indicator housing 27 and/or retaining part 29.

According to one aspect, the height or axial extension of the indicator device 25 or its housing 27 corresponds preferably at least essentially to the length of the lifting/stroke movement of the container 3. In this way, a very compact construction of the nebulizer 1 can be achieved and/or the available space within in the nebulizer 1 can be utilized optimally or to a maximum.

Preferably, the length of the stroke movement and/or the height of the indicator device 25 or housing 27 is at least 5 mm, in particular at least 7 mm, particularly preferably at least 8.5 mm, and/or at most 30 mm, in particular at most 15 mm, particularly preferably at most 9.5 mm.

In the loaded state of the nebulizer 1, the container 3 preferably only protrudes with its container base 3A out of the indicator device 25 or indicator housing 27, as shown in FIGS. 3 and 4. However, the container base 3A may also be flush with the indicator device 25 or indicator housing 27 in the loaded state. For ease of insertion, it is therefore preferred that the container 3 is inserted into the nebulizer 1 in the loaded state of the nebulizer 1.

As already mentioned above, the nebulizer 1 preferably comprises a drive device 23, in particular for driving or actuating the locking device 24 and/or indicator device 25.

The indicator element 26 is preferably driven by the drive device 23 or its shaft 30. In particular, the drive device 23 or shaft 30 is adapted to index the indicator element 26 or to rotate it one step further when the nebulizer 1 is actuated or loaded.

Preferably, the drive device 23 acts as a transmission, in particular such that the rotation of the inner part 17 relative to the upper housing part 16 for loading the nebulizer 1 or energy store 7 causes an indexing of the indicator element 26, transmitted via the drive device 23.

Particularly preferably, the drive device 23 is adapted to drive or actuate both the indicator element 26 and the locking device 24. However, also solutions are possible in which the drive device 23 only drives or actuates the indicator element 26. The locking device 24 may then be driven or actuated by different means. Alternatively, no locking device 24 or no locking of the nebulizer 1 may be provided.

Figures 7, 8:
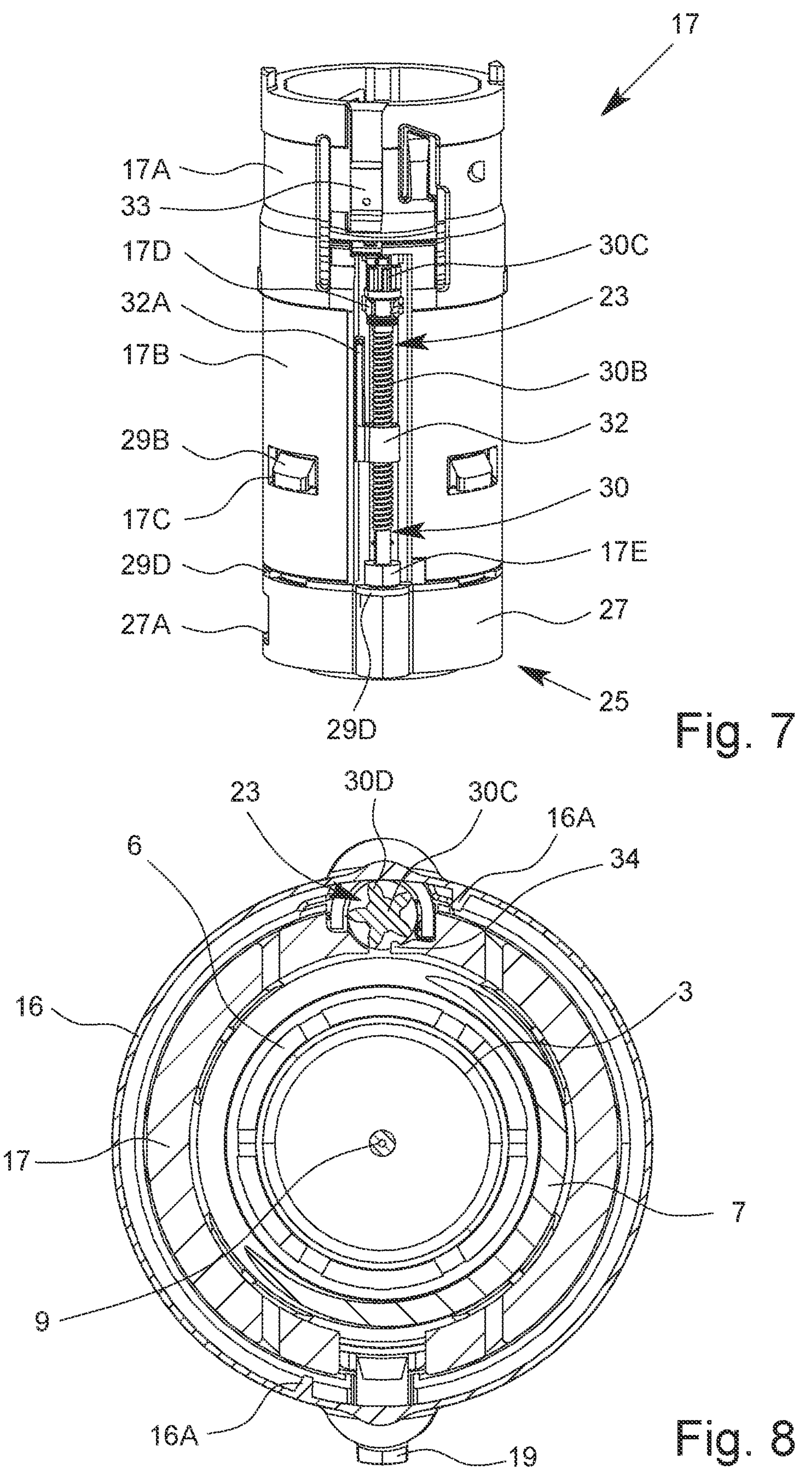
FIG. 7 is a schematic side view of an inner part of the proposed system/nebulizer with attached indicator device.
FIG. 8 is a schematic section along line VIII-VIII in FIG. 4.

In the following, the drive device 23 and its preferred coupling with the indicator element 26 is explained in more detail, in particular with reference to FIGS. 6 and 7. FIG. 6 shows the proposed nebulizer 1 in a view similar to FIG. 3, but without container 3, lower housing part 18, indicator housing 27 and drive device cover 28. FIG. 7 shows a schematic side view of the inner part 17 with attached drive device 23 and indicator device 25.

The drive device 23 is preferably formed by or comprises the shaft 30.

In the assembled state, the shaft 30 preferably extends in the axial direction and/or at least essentially parallel to the axis A. Preferably, the shaft 30 extends or is located laterally at the nebulizer 1, in particular the inner part 17. Particularly preferably, the shaft 30 extends at least essentially along the entire (axial) length of the lower inner part 17B.

The shaft 30 is preferably attached, in particular clipped, to the inner part 17 or its lower part 17B. The inner part 17 preferably comprises one or more holding portions 17D for holding the shaft 30 at the inner part 17. In particular, the one or more holding portions 17D may be embodied as protrusions into which the shaft 30 can be clipped, as for example shown in FIG. 7.

The one or more holding portions 17D are preferably embodied as holding arms and/or are fork-like. Preferably, the holding portions 17D are flexible and/or are chamfered and/or comprise (each) a lead-in chamfer, in particular for facilitating the clipping or insertion of the shaft 30.

Preferably, the shaft 30 is axially and/or radially supported and/or fixed by the one or more holding portions 17D.

The inner part 17, in particular its lower part 17B, preferably forms or comprises a bearing lug 17E for (radially and/or axially) bearing the shaft 30. In particular, the shaft 30 is (radially and/or axially) supported by the inner part 17 or bearing lug 17E, in particular from the sides and/or below.

Preferably, the shaft 30 reaches through the bearing lug 17E and/or extends to the other side of the bearing lug 17E, in particular with its (lower) free or axial end and/or with a portion 30A. The portion 30A is preferably thinned such that axial bearing of the shaft 30 at the bearing lug 17E is facilitated. In particular, only the thinned portion 30A fits through the bearing lug 17E. However, it is also possible that the shaft 30 does not comprise the thinned portion 30A and/or is borne only radially by the bearing lug 17E.

Particularly preferably, the shaft 30 is held or supported rotatably at the inner part 17, in particular by means of the one or more holding portions 17D and/or the bearing lug 17E. In other words, the shaft 30 is preferably rotatable around its longitudinal axis when attached to the nebulizer 1 or inner part 17.

However, also solutions are possible in which only holding portions 17D are provided and/or the bearing lug 17E is omitted. Preferably, in this case, the shaft 30 is (rotatably) held at both axial ends by means of the holding portions 17D.

Additionally, the drive device cover 28 may form a bearing or support for the shaft 30.

The drive device 23 or shaft 30 preferably comprises a drive gear 31 for driving, rotating or indexing the indicator element 26.

The drive gear 31 is preferably a separate part which can be plugged or clipped to the shaft 30 or can be attached at the shaft 30 in another way. However, also solutions are possible in which the drive gear 31 forms part of the shaft 30 or is integrally formed therewith, in particular injection-molded to the shaft 30.

The drive gear 31 is preferably located at or attached to the lower free or axial end of the shaft 30, in particular the (thinned) portion 30A. In particular, the drive gear 31 can be plugged onto the portion 30A.

The drive gear 31 is preferably attached or coupled to the shaft 30 in a rotatably fixed manner with respect to the shaft 30. In other words, the drive gear 31 is preferably rotatable together with the shaft 30.

The shaft 30 is preferably held or secured in an axially and/or radially defined position, in particular by means of the bearing lug 17E and/or drive gear 31 and/or holding portion(s) 17D.

Particularly preferably, the drive device 23 or shaft 30 is non-detachably attached to or connected with the inner part 17.

The indicator housing 27 preferably comprises a receiving portion 27C for receiving or accommodating the drive gear 31. In particular, in the assembled state, the drive gear 31 is preferably located inside the indicator housing 27.

Preferably, the retaining part 29 or the connection portion 29D, in particular a protrusion for connecting with the receiving portion 27C, comprises an opening 29E through which the drive device 23, shaft 30 and/or drive gear 31 can reach into the indicator device 25, in particular the indicator housing 27 or its receiving portion 27C.

In the following, a preferred method for (partial) assembly the nebulizer 1 will be described. Individual steps may be omitted or performed in a different order.

Preferably, in a first step, the inner part 17 is assembled by inserting the energy store 7 or drive spring and retaining it with the retaining part 29.

Preferably, in a second or further step, the drive device 23 or shaft 30 is attached to the inner part 17. This is preferably performed by first inserting the shaft 30 with its (lower) free or axial end into the bearing lug 17E and then clipping it into the one or more holding portions 17D, in particular with a pivot movement.

Particularly preferably, the shaft 30 is first attached to the inner part 17, in particular as described above by means of the holding portions 17D and/or bearing lug 17E, and then the drive gear 31 is attached to, in particular plugged onto, the shaft 30, in particular its thinned portion 30A, particularly preferably from below. Preferably, the shaft 30 is first inserted or guided, in particular with its thinned portion 30A, through the bearing lug 17E and is then secured from below by the drive gear 31.

However, also other solutions are possible here. For example, if the bearing lug 17E is omitted, as explained above, the drive gear 31 can be secured at the shaft 30 before attaching the shaft 30 at the nebulizer 1 or inner part 17, in particular by clipping it into the holding portions 17D. In this case, the drive gear 31 may also be integrally formed with the shaft 30.

Preferably, in a third or further step, the upper housing part 16 is attached to or combined with the inner part 17, in particular in a non-detachable manner. This step is preferably performed after attaching the drive device 23 or shaft 30 to the inner part 17. In this way, the drive device 23 and/or shaft 30 is preferably secured by the upper part 16 and/or removal of the drive device 23 and/or shaft 30 is prevented or is not possible anymore.

Preferably, in a fourth or further step, the indicator device 25, indicator element 26 and/or indicator housing 27 is attached to the nebulizer 1 or inner part 17, in particular the retaining part 29 or its connection portion(s) 29D, after the drive device 23 or shaft 30 has been attached to the nebulizer 1 or inner part 17, particularly preferably after the drive gear 31 has been attached to the shaft 30.

In a fifth or further or final step, the container 3 may be inserted and/or the lower housing part 18 may be attached.

Preferably, the indicator element 26 is first placed at the nebulizer 1 or inner part 17, in particular at the retaining part 29 or its support portion 29C, and is then secured by means of the indicator housing 27.

Preferably, the shaft 30 or drive gear 31 is first attached the nebulizer 1 or inner part 17, as explained above, and is then secured by means of the indicator housing 27.

The indicator housing 27 is preferably attached to nebulizer 1 or inner part 17, in particular the retaining part 29 or its connection portion(s) 29D, in a non-detachable manner, for example by ultrasonic welding, as explained above.

Preferably, by means of the non-detachable indicator housing 27, both the indicator device 25/indicator element 26 and the shaft 30 are non-detachably attached to the nebulizer 1 and/or to the inner part 17 and/or to each other.

Particularly preferably, the indicator device 25 or its indicator element 26 is non-detachably attached to or connected or operatively coupled with the drive device 23 or shaft 30 or its drive gear 31.

The indicator element 26 preferably comprises or forms an indicator gear or toothing 26B.

The toothing 26B is preferably provided around the circumference of the indicator element 26, in particular on the outer side (forming an external toothing). However, it is also possible to provide the toothing 26B on the inner side of the indicator element 26 (forming an internal toothing).

The teeth of the toothing 26B preferably protrude in the radial direction, in particular such that along the circumference of the indicator element 26 teeth and gaps alternate. Preferably, the teeth extend in the axial direction and/or are aligned parallel to the axis of rotation of the indicator element 26.

Particularly preferably, the indicator element 26 or toothing 26B is embodied as or forms a spur gear or toothed wheel.

The toothing 26B is preferably integrally formed with or by the indicator element 26.

The drive device 23, in particular the drive gear 31, preferably meshes with the indicator element 26 or its toothing 26B, in particular permanently. In particular, the drive gear 31 and toothing 26B not only mesh when the nebulizer 1 is actuated, but also between two actuations.

The drive gear 31 preferably comprises a corresponding toothing and/or corresponding teeth, which in particular protrude in the radial direction and/or extend in the axial direction and/or are aligned parallel to the axis of rotation of the drive gear 31. In particular, the drive gear 31 is embodied as or forms a spur gear.

The meshing is preferably such that the teeth of the toothing 26B and of the drive gear 31 extend parallel to each other in the axial direction and/or such that the drive gear 31 is located besides the (outer) circumference or outside of the indicator element 26.

As already mentioned above, the toothing 26B may be provided on the inner circumference of the indicator element 26, in which case the drive gear 31 is located at the inner circumference or inside of the indicator element 26. However, this renders the construction more complex, such that the variant with toothing 26B on the outer circumference is preferred.

In principle, also other solutions for the meshing and/or the arrangement of the toothing 26B and/or the drive gear 31 are possible. For example, the toothing 26B may be embodied as a saw toothing, with the saw teeth protruding in the axial direction and the drive gear 31 being located axially above the indicator element 26 for meshing. However, the above described variant with radially protruding teeth on the outer circumference is preferred since it allows for a more precise transmission and/or a particularly simple and/or compact arrangement and/or assembly.

Preferably, the indicator element 26 and the shaft 30 are rotatably coupled with each other, in particular via the drive gear 31 and the toothing 26B.

Preferably, the drive device 23/shaft 30 and indicator element 26, in particular the drive gear 31 and toothing 26B, form a gear reduction. This means that the rotational speed of the drive device 23, in particular of the shaft 30 or drive gear 31, is higher than that of the indicator element 26 or toothing 26B. In particular, a full revolution/turn of the shaft 30 or drive gear 31 results in only a partial revolution/turn of the indicator element 26, for example a rotation of about 30°.

However, it is noted that for indexing or rotating the indicator element 26 one step further, preferably only a partial revolution/turn of the shaft 30 is required. When the shaft 30 has performed a full or complete revolution/turn, the nebulizer 1 has preferably been actuated more than once and/or the indicator element 26 has preferably already been indexed more than once, e.g. five or six times.

A full or complete revolution/turn is to be understood as a rotation by 360°. Accordingly, a half revolution or half turn is to be understood as a rotation by 180°.

The so-called gear ratio is a measure for the gear reduction and specifies how a movement of the driving gear affects the movement of the driven gear. In particular, it can be deduced from the gear ratio by what angle the driven gear rotates when the driving gear is rotated by a given angle. In other words, the gear ratio may be defined as the ratio of said angles.

The gear ratio may be used to determine how many full revolutions/turns of the driving gear are necessary to cause one full revolution/turn of the driven gear.

For example, a gear ratio of 10:1 implies that ten complete revolutions/turns of the driving gear, in the present case of the drive gear 31, would result in or would be equivalent to one complete revolution/turn of the driven gear, in the present case the indicator element 26 with toothing 26B. It also implies that one full turn of the driving gear would result in a tenth of a full turn of the driven gear, i.e. in a rotation by about 36°.

It should be noted that there are different ways to represent the gear ratio, for example the gear ratio 5:2 is equivalent to the gear ratio 2.5:1 and implies that two full turns and one half turn of the driving gear cause one full turn of the driven gear or, equivalently, that five full turns of the driving gear cause two full turns of the driven gear.

One way to calculate the gear ratio is to divide the number of teeth of the driven gear by the number of teeth of the driving gear. If the teeth are equally distributed, this is equivalent to dividing the diameter of the driven gear by the diameter of the driving gear.

It should be noted that the actual number of teeth or the actual diameters can usually not be read off from the gear ratio since it is usually given as a reduced fraction. For example, a gear ratio 10:1 could be achieved by a teeth ratio or diameter ratio of 50:5, 100:10, etc.

In the present case, the gear ratio of the indicator element 26 with toothing 26B to the drive gear 31 (in the following referred to as first gear ratio) is given by the ratio of the teeth of the toothing 26B to the number of teeth of the drive gear 31, and/or by the ratio of the diameter of the toothing 26B to the diameter of the drive gear 31, and/or by the angle ratio which determines by what angle the indicator element 26 rotates when the drive gear 31 is rotated by a given angle.

The gear reduction is in particular achieved by the drive gear 31 having fewer teeth than the toothing 26B and/or by the drive gear 31 having a smaller diameter than the toothing 26B. The desired gear ratio can preferably be set by adjusting the number of teeth and/or the diameters of the toothing 26B and the drive gear 31.

The first gear ratio is preferably smaller than 30:1, in particular smaller than 20:1 or 15:1 and/or is larger than 5:1, in particular larger than 10:1.

Preferably, the loading or tensioning of the nebulizer 1 or the rotation of the inner part 17 relative to the upper housing part 16 drives the shaft 30 and, thus, preferably indirectly also the indicator element 26. This driving of the shaft 30, in particular by means of a gear reduction, will be explained later in connection with FIG. 8.

As already indicated above, the drive device 23, in addition to driving the indicator element 26, is preferably embodied to drive the locking device 24 for locking the nebulizer 1 against further use. This will be explained in more detail in the following.

The drive device 23, in particular the shaft 30, preferably comprises a threaded portion 30B, with an associated rider 32. When rotating the shaft 30, the rider 32 is axially moved, here upwards.

The rider 32 comprises preferably an actuation portion 32A. The actuation portion 32A is preferably ridge-like and/or extending in axial direction and/or towards the upper housing part 16 and/or upwards.

When the nebulizer 1 reaches or exceeds a predetermined value of operations or actuations, the drive device 23 or the actuation portion 32A of the rider 32 can actuate the locking device 24 to lock the nebulizer 1 against further operation or use, in particular by interlocking the inner part 17 with the upper housing part 16 or vice versa.

The locking is preferably realized in the shown embodiment in that the actuation portion 32A of the rider 32 cooperates with or actuates a locking spring 33 of the locking device 24, in particular axially shifts the locking spring 33 (upwards). The locking spring 33 is mounted in a pre-tensioned state such that it can radially expand and engage into a radial recess or the like, in particular of the upper housing part 16, when the locking spring 33 or part thereof is actuated or axially shifted (here by the rider 32 or its actuation portion 32A) to lock the nebulizer 1 or interlock its parts 16 and 17. However, other constructional solutions are possible as well.

The nebulizer 1 or locking device 24 preferably provides a live span blocking when the total number of actuations of the nebulizer 1 has reached or exceeded the predetermined value. The blocking is realized in the present embodiment by the locking spring 33 which finally locks the nebulizer 1 against further use, in particular against further loading or tensioning.

Since the rider 32 moves further (upwards) along the shaft 30 with each actuation of the nebulizer 1, its axial position corresponds (roughly) to the number of actuations. Thus, the drive device 23 or rider 32 may form a second indicator device.

The drive device 23 or its rider 32, in particular the axial position of the rider 32 along the shaft 30, may show or indicate (roughly) the (total) number of operations, in particular of loading, actuations or doses, which have already been performed or used with the nebulizer 1 or which can still be performed with the nebulizer 1. This may in particular be shown by a pointer of the rider 32 and/or an associated scale or the like (not shown) which are visible through a corresponding window or transparent part of the lower housing part 18.

It has to be noted that the number has not to be shown precisely. In particular, it may be sufficient that the drive device 23 or the rider 32 give a rough indication of the number. For this purpose, it may be sufficient if the scale shows only different colored areas or regions roughly indicating said number. Thus, the drive device 23 may be used to give a rough indication while the indicator device 25 may give a more precise indication or counting.

However, in a preferred embodiment (as is also shown in the figures), the rider 32 is provided only for actuating the locking device 24. In particular, indicating or counting is only performed by the indicator device 25. In this case, the rider 32 is preferably non-visible or covered, in particular by the drive device cover 28. This has the advantage that the nebulizer 1 comprises additional surface area that can be used for labeling or the like, which surface area would otherwise need to remain uncovered for visibility of the second indicator device.

Also other solutions for locking the nebulizer 1 and/or forming a locking device 24 are possible. In particular, the indicator element 26 could be blocked after the last actuation, preferably after the indicator element 26 has performed at least essentially a full turn or revolution. For example, the indicator element 26 may comprise a recess into which a locking spring or a protrusion or the like engages when the indicator element 26 reaches its final position or is indexed for the last time, thus blocking the indicator element 26 from further rotation/indexing. Blocking of the indicator element 26 preferably also blocks the shaft 30 from being rotated which, in turn, blocks rotation of the upper housing part 16 relative to the inner part 17.

In the following, the drive mechanism for the shaft 30 will be explained in more detail, in particular with reference to FIG. 8 which is a schematic section of the nebulizer 1 along line VIII-VIII shown in FIG. 4.

The drive device 23 or shaft 30 preferably comprises a shaft gear 30C.

The shaft gear 30C is preferably located at the free or axial end of the shaft 30 opposite the drive gear 31, in particular the upper free or axial end.

The shaft gear 30C is preferably formed by the shaft 30 or integrally formed therewith. However, other constructional solutions are possible as well, in which the shaft gear 30C is embodied as a separate component fixed to the shaft 30. For example, the shaft gear 30C may be plugged onto the shaft 30 similar to the drive gear 31.

The shaft gear 30C is preferably constructed or arranged to mesh with the upper housing part 16 so that the shaft 30 is rotated when the nebulizer 1 is loaded/tensioned, in particular when the inner part 17 (together with the shaft 30) is rotated relative to the upper housing part 16.

The nebulizer 1, in particular the upper housing part 16, preferably comprises one or more drive portions 16A which cooperate or mesh with the shaft gear 30C when the nebulizer 1 is loaded/tensioned, preferably each time the nebulizer 1 is loaded/tensioned or at least every second time the nebulizer 1 is loaded/tensioned.

Preferably, the meshing of the drive portion(s) 16A and shaft gear 30C is only temporarily and/or non-permanent and/or only when the nebulizer 1 is actuated. In particular, the drive portion(s) 16A do not engage or mesh with the shaft gear 30C between two actuations.

Preferably, the shaft 30 or shaft gear 30C is associated with the inner part 17 and the one or more drive portions 16A are associated with the upper housing part 16. Therefore, when the inner part 17 and upper housing part 16 are rotated relative to each other, the drive portions 16A and the shaft gear 30C are preferably also rotated relative to each other.

Preferably, the number and/or position of the drive portions 16A are/is such that for each loading, (exactly) one of the drive portions 16A meshes with the shaft gear 30C. However, also other solutions are possible in which more than one drive portion 16A meshes or cooperates with the shaft gear 30C during one loading process or in which, for example, only every second loading causes driving of the shaft 30.

Preferably, the number and/or position of the drive portions 16A corresponds to the angle by which inner part 17 and upper housing part 16 are to be rotated relative to each other for loading the nebulizer 1. For example, if a full turn is necessary, only one drive portion 16A is preferably provided.

In the embodiment shown, loading of the nebulizer 1 is preferably performed by rotating inner part 17 and upper housing part 16 relative to each other by half a turn, i.e. by around 180°. Correspondingly, the nebulizer 1 or upper housing part 16 preferably comprises two drive portions 16A located on opposite sides of the upper housing part 16. In this way, (exactly) one drive portion 16A meshes or cooperates with the shaft gear 30C with each loading process. However, also other solutions are possible. In particular, only one drive portion 16A may be provided such that only every second actuation/half turn results in a rotational movement of the shaft 30 and, consequently, of the indicator element 26.

Preferably, the drive portions 16A are arranged or positioned such that the meshing/cooperating with the shaft gear 30C or rotation of the shaft 30 is only performed at the end of the loading process. In this way, it is ensured that the shaft 30 is only rotated when the nebulizer 1 has been fully loaded. Thus, an actuation is preferably only counted when the loading has been completed.

In the example shown in FIG. 8, the upper housing part 16 is rotated clockwise for half a turn for loading the nebulizer 1. The shown drive portions 16A thus only cooperate/mesh with the shaft gear 30C and/or rotate/index the shaft 30 shortly before the half turn has been completed.

In the embodiment shown, the drive portions 16A are preferably formed by in particular inwardly extending protrusions of the upper housing part 16. When the upper housing part 16 is rotated relative to the inner part 17, one of the protrusions, in FIG. 8 the protrusion which is located at least essentially opposite the shaft gear 30C, will engage, mesh or cooperate with the drive portion 30C.

Preferably, the shaft 30 is rotated or indexed by a defined angle when loading the nebulizer 1, in particular each time or at least every second time the nebulizer 1 is loaded.

In the example shown, the shaft gear 30 preferably comprises a plurality of radial protrusions or teeth 30D. In particular, in a section, the shaft gear 30C has the shape of a star. The drive portion 16A can preferably engage between two protrusions/teeth 30D.

Actuation of the nebulizer 1, in particular loading of the energy store 7, preferably causes a partial rotation/revolution/turn of the shaft 30, i.e., by less than 360°, particularly preferably by about 360° divided by the number of teeth 30D.

The drive mechanism for driving the shaft 30 forms preferably a gear reduction. In particular, the gear ratio for driving the shaft 30 (in the following referred to as second gear ratio) is given by the ratio of a full turn of the upper housing part 16 to the angle by which the shaft 30 has rotated after such full turn of the upper housing part 16, and/or by the number of teeth 30D to the number of drive portions 16A.

Preferably, the second gear ratio is at least 3:2 or 4:1 and/or at most 6:1 or 7:1.

In the specific example shown in FIG. 8, the shaft gear 30C preferably comprises five teeth 30D. Accordingly, five or ten actuations preferably cause a full revolution/turn of the shaft 30. In particular, the second gear ratio is 5:2 or 5:1. In other, words, five half turns or five full turns of the upper housing part 16, corresponding to five or ten actuations of the nebulizer 1, cause preferably one full revolution/turn of the shaft 30. However, also other solutions are possible.

In a particularly preferred embodiment (not shown), the shaft gear 30C comprises six teeth 30D. Accordingly, six or twelve actuations preferably cause a full revolution/turn of the shaft 30. In particular, the second gear ratio is 6:2 or 6:1. In other words, six half turns or six full turns of the upper housing part 16, corresponding to six or twelve actuations of the nebulizer 1, cause preferably one full revolution/turn of the shaft 30.

Preferably, the second gear ratio, the first gear ratio and/or the pitch of the threaded portion 30B are matched with respect to each other.

In particular, the first and second gear ratios are matched such that rotation of the upper housing part 16 relative to the inner part 17, in particular by a half turn, causes an indexing of the indicator element 26 by one step or to the next number. For example, in the case of the nebulizer 1 being adapted for nebulization of 60 doses of fluid 2, the rotation of the upper housing part 16 relative to the inner part 17 preferably causes at least essentially or at most a rotation of 6° or of 1/60 of a full turn of the indicator element 26, such that the indicator element 26 has been rotated by at least essentially or less than 360° after nebulization of all 60 doses.

More generally, the first and second gear ratios are preferably matched such that the indicator element 26 has performed at least essentially a full turn/revolution when the total number of doses of fluid 2 has been used/nebulized. However, also solutions are possible in which the indicator element 26 has performed only a partial turn/revolution or has been rotated less than 360° when the total number of doses of fluid 2 has been used/nebulized.

Particularly preferably, if each actuation of the nebulizer 1 involves a half turn of the upper housing part 16 relative to the inner part 17, the product of the first and second gear ratio is at least essentially half the total number of doses of fluid 2. In this way, it is ensured that the indicator element 26 has performed at least essentially one revolution/turn when the total number of doses of fluid 2 has been nebulized.

More generally, actuation of the nebulizer 1 preferably causes a partial rotation of the shaft 30, in particular by a defined angle, and this partial rotation indexes the indicator element 26 one step further and/or causes a partial rotation of the indicator element 26, in particular by a (different) defined angle.

The pitch of the threaded portion 30B is preferably adapted or matched such that the rider 32 actuates the locking device 24 after the last dose of fluid 2 has been nebulized or when the indicator element 26 has performed at least essentially a full turn.

The nebulizer 1, in particular the inner part 17 or the upper housing part 16, preferably comprises a positioning device 34, as shown in FIG. 8.

Preferably, the positioning device 34 keeps the shaft 30 in a defined rotational position, in particular between two actuations of the nebulizer 1 and/or when the nebulizer 1 is not actuated or used and/or in the closed or (fully) assembled state and/or in the unloaded state and/or in the loaded state of the nebulizer 1.

Particularly preferably, the positioning device 34 keeps the shaft 30 or shaft gear 30C in a respective defined rotational position both before and after actuation and/or allows rotational movement of the shaft 30 or shaft gear 30C only during actuation.

The positioning device 34 preferably holds the shaft 30 or shaft gear 30C in a defined (rotational) position by engaging and/or latching with the shaft 30 or shaft gear 30C.

Preferably, the shaft gear 30C, in particular its teeth 30D, are held in a defined (rotational) position by means of the positioning device 34 such that engagement or meshing with the drive portion 16A is (always) possible when the nebulizer 1 is actuated.

In particular, in an undefined position, it might happen that the shaft gear 30C, in particular the teeth 30D, and the drive portion 16A are positioned relative to each other such that the drive mechanism becomes blocked or stuck, e.g. when the drive portion 16A drives against a front face of a tooth 30D instead of engaging or meshing between two teeth 30D. This is preferably prevented by means of the positioning device 34.

Moreover, in an undefined position, it might happen that the teeth 30D and drive portion 16A do not mesh as desired, but instead collide with each other. In the worst case, this might lead to a tooth 30D or drive portion 16A to break off. This is preferably prevented by means of the positioning device 34.

Particularly preferably, the positioning device 34 blocks the shaft 30 from rotating backwards or acts as or is a non-return device or return stop.

The positioning device 34 may for example be embodied as or comprise a projection, in particular of the inner part 17, which engages or latches between two teeth 30D of the shaft gear 30C, blocking a rotation in the direction opposite to the drive direction.

Preferably, the positioning device 34 also blocks rotation of the shaft 30 in the drive direction. When the nebulizer 1 is actuated, in particular when the upper housing part 16 is rotated relative to the inner part 17, said blocking is preferably overcome or the positioning device 34 is adapted therefor. For example, the positioning device 34 may be embodied to flex away when the shaft 30 is rotated, preferably such that (exactly) one tooth 30D can pass the positioning device 34.

Particularly preferably, the positioning device 34 is embodied or acts as a ratchet or pawl.

Preferably, a ratchet and/or a pawl and/or the positioning device 34 allows rotary motion of the shaft 30 in only one direction while preventing motion in the opposite direction.

By means of the positioning device 34, it is preferably prevented that the indicator element 26 is indexed backwards and/or that the rider 32 moves in the downward direction or in the direction away from the locking device 24.

The positioning device 34 is preferably integrally formed with or formed by the inner part 17 or the upper housing part 16.

The positioning device 34 is preferably embodied as a flexible arm and/or protruding rib and/or preferably extends in the axial direction, particularly preferably along at least essentially the entire axial length of the shaft gear 30C or its teeth 30D.

The flexible arm and/or protruding rib preferably forms the ratchet and/or pawl.

In a different embodiment (not shown), the positioning device 34 may be located at the lower end of the shaft 30, in particular may cooperate or engage with the drive gear 31 and/or the indicator element 26 or its toothing 26B. For example, the positioning device 34 may be formed by the housing 27 in this case.

The proposed nebulizer 1 can preferably only be used with one container 3. In this way, it is preferably possible to adjust or tune the counting and/or indicating precisely to the number of doses contained. However, also solutions are possible in which multiple containers 3 are usable with the nebulizer 1. In this case, the drive device 23 and/or locking device 24 are preferably adapted such that the nebulizer 1 reaches its live span blocking only after a predetermined number of containers 3 has been used, for example three or four containers 3.

Preferably, in the case of the nebulizer 1 being adapted for use with multiple containers 3, the indicator device 25 is adapted accordingly to count or indicate the total number of actuations or uses of the nebulizer 1 with multiple containers 3. In particular, one full turn/revolution of the indicator element 26 corresponds to the total number of operations possible with the maximum number of containers 3 before the nebulizer 1 reaches the live span blocking.

Alternatively, the indicator device 25 may be resettable or adapted to count the number of actuations or uses with the current container 3. In particular, one full turn/revolution of the indicator element 26 corresponds to the total number of operations possible with one container 3. When the container 3 needs to be changed, the indicator element 26 has preferably performed one full turn/revolution and/or is (again) in its initial state (the state before first use with the current container 3) such that it can be used with a new container 3.

However, as already mentioned above, the indicator device 25 is preferably permanently fixed to the nebulizer 1 or inner part 17 and/or cannot be removed from the nebulizer 1 or inner part 17 and/or cannot be replaced or exchanged, even if an exchange of the container 3 is possible.

Generally, it should be pointed out that in the proposed nebulizer 1, the container 3 can preferably be inserted into the nebulizer 1. Consequently, the container 3 is preferably a separate component. However, the container 3 may theoretically be formed directly by part of the nebulizer 1 or its housing part 18 or may otherwise be integrated in the nebulizer 1 or its housing part 18, in particular when the nebulizer 1 is to be used with one container 3 only.

Individual features, aspects and/or principles described can be realized independently from each other or in any combination.

Unlike free standing equipment or the like, the proposed nebulizer 1 is preferably designed to be portable and in particular is a mobile hand operated device.

Preferably, the fluid 2 is a liquid, as already mentioned above, especially an aqueous pharmaceutical formulation or an ethanolic pharmaceutical formulation, in particular having polar characteristics. However, the fluid 2 may also contain other pharmaceutical formulations, a suspension or the like, preferably based on water or ethanol.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary, the fluid 2 may also be atomized by means of a propellant gas.

Preferred ingredients and/or formulations of the preferably medicinal fluid 2 are listed in particular in WO 2009/115200 A1, in particular on pages 25 to 40, or in EP 2 614 848 A1, paragraphs 0040 to 0087, which are incorporated herewith by reference. Preferably, these ingredients/formulations may be aqueous or non-aqueous solutions, mixtures, formulations containing in particular ethanol and/or being free from any solvent or the like.

LIST OF REFERENCE SIGNS

1 nebulizer
2 fluid
3 container
3A container base
3B venting hole
4 reservoir
5 fluid pump
6 holder
7 energy store
8 blocking element
8A release button
9 connecting element
10 non-return valve
11 pressure chamber
12 nozzle
13 mouthpiece
14 aerosol
15 air supply opening
16 upper housing part
17 inner part
17A upper inner part
17B lower inner part
17C recess
17D holding portion
17E bearing lug
18 lower housing part
19 retaining element
20 piercing element
21 aeration spring
22 mouthpiece cover
23 drive device
24 locking device
25 indicator device
26 indicator element
26A markings
26B toothing
27 indicator housing
27A window
27B pointer
27C receiving portion
28 drive device cover
29 retaining part
29A bearing surface
29B flexible arm
29C support portion
29D connection portion
29E opening
30 shaft
30A thinned portion
30B threaded portion
30C shaft gear
30D tooth
31 drive gear
32 rider
32A actuation portion
33 locking spring
34 positioning device
A axis

The invention claimed is:

1. A nebulizer for nebulizing a fluid, comprising:
a container with a container housing containing the fluid,
an inner part in which the container is received,
a holder moveably positioned within the inner part for holding the container,
a detachable housing part which is detachable from the inner part,
an indicator device with a rotatable indicator element for counting or indicating a number of actuations performed or still possible with the nebulizer, and a rotatable shaft which is configured to rotatably drive the indicator element,
wherein the indicator device comprises an indicator housing,
wherein the indicator device is separate from the container and wherein the indicator housing is non-detachably attached to an end of the inner part, and
wherein the detachable housing part is configured to receive the end of the inner part and the indicator device such that the detachable housing part, the holder, and the inner part cooperate to enclose the container during use and the detachable housing part encircles the indicator device.

2. The nebulizer according to claim 1, wherein the nebulizer comprises an energy store disposed in the inner part for providing energy to nebulize the fluid, wherein the inner part comprises a retaining part which retains, bears or biases the energy store, wherein at least one of:
the indicator device is attached to the retaining part;
the indicator element encompasses the retaining part or a support portion thereof; and
the retaining part forms a rotation bearing for the indicator element.

3. The nebulizer according to claim 1, wherein:
the container is configured to execute a stroke movement when the nebulizer is actuated, and
a height of the indicator device or the indicator housing corresponds at least essentially to a length of the stroke movement.

4. The nebulizer according to claim 1, wherein at least one of:
the indicator element comprises or forms a toothing,
the indicator element is ring-like, and
the indicator element is embodied as or forms a spur gear and/or toothed wheel.

5. The nebulizer according to claim 1, wherein
the indicator housing comprises a window such that the indicator element is partly visible.

6. The nebulizer according to claim 1, wherein the shaft is provided with a drive gear which rotatably couples the shaft with the indicator element, wherein the nebulizer or inner part comprises or forms a bearing lug for the shaft, the shaft reaching through the bearing lug with a portion which is provided with the drive gear.

7. The nebulizer according to claim 1, wherein the nebulizer comprises a rider and wherein the shaft comprises a threaded portion for linearly driving the rider, wherein the rider forms a second indicator device and/or is configured to actuate a locking device locking the nebulizer against further actuation when a predetermined number of actuations has been reached or exceeded.

8. The nebulizer according to claim 1, wherein the nebulizer comprises one or more drive portions configured to cooperate with the shaft or a shaft gear thereof when the nebulizer is actuated such that the shaft is rotated by a defined angle, wherein the nebulizer comprises an upper housing part, wherein the nebulizer is configured to be actuated by rotating the inner part relative to the upper housing part, and wherein the one or more drive portions are formed by one or more teeth of the upper housing part.

9. The nebulizer according to claim 1, wherein the shaft is attached to the inner part and extends along the inner part.

10. The nebulizer according to claim 1, wherein the nebulizer comprises a positioning device configured to keep the shaft in a defined rotational position between two actuations and/or to act as a ratchet.

11. The nebulizer according to claim 1, wherein the container is configured to execute a stroke movement relative to the indicator device when the nebulizer is actuated.

12. A nebulizer for nebulizing a fluid, comprising:

a container with a container housing containing the fluid, an inner part in which the container is received, a holder moveably positioned within the inner part for holding the container, a detachable housing part which is detachable from the inner part, an indicator device with a rotatable indicator element for counting or indicating a number of actuations performed or still possible with the nebulizer, a rotatable shaft which is configured to rotatably drive the indicator element, and a positioning device on the inner part configured to keep the shaft in a defined rotational position between two actuations and/or to act as a ratchet, wherein the indicator device comprises an indicator housing, wherein the indicator device is separate from the container and wherein the indicator housing is non-detachably attached to an end of the inner part, and wherein the detachable housing part is configured to receive the end of the inner part and the indicator device such that detachable housing part, the holder, and the inner part cooperate to enclose the container during use and the detachable housing part encircles the indicator device.

13. The nebulizer according to claim 12, wherein the positioning device is embodied as or comprises a flexible arm, a projection or ratchet which engages between two teeth of a shaft gear of the shaft.

14. The nebulizer according to claim 12, wherein the positioning device is embodied as a ratchet to flex away when the shaft is rotated, allowing rotary motion of the shaft in only one direction while preventing motion in the opposite direction.

15. The nebulizer according to claim 12, wherein the positioning device is integrally formed with or formed by the inner part.

16. The nebulizer according to claim 12, wherein the container is configured to execute a stroke movement relative to the indicator device when the nebulizer is actuated.

17. A nebulizer for nebulizing a fluid, comprising:

a container with a container housing containing the fluid, the container being configured to execute a stroke movement relative to an indicator device when the nebulizer is actuated, an inner part in which the container is received, a holder moveably positioned within the inner part for holding the container, a detachable housing part which is detachable from the inner part, the indicator device having a rotatable indicator element for counting or indicating a number of actuations performed or still possible with the nebulizer, and a rotatable shaft which is configured to rotatably drive the indicator element, wherein the indicator device comprises an indicator housing, wherein the indicator device is separate from the container and wherein the indicator housing is non-detachably attached to an end of the inner part, wherein the detachable housing part is configured to receive the free end of the inner part and the indicator device such that detachable housing part, the holder, and the inner part cooperate to enclose the container during use and the detachable housing part encircles the indicator device, and wherein a height of the indicator device or the indicator housing of the indicator device corresponds at least essentially to the length of the stroke movement.

18. The nebulizer according to claim 17, further comprising a positioning device configured to keep the shaft in a defined rotational position between two actuations and/or to act as a ratchet.

* * * * *